US008574864B2

(12) United States Patent
Vaidyanathan et al.

(10) Patent No.: US 8,574,864 B2
(45) Date of Patent: Nov. 5, 2013

(54) METHODS AND KITS FOR 3'-END-TAGGING OF RNA

(75) Inventors: Ramesh Vaidyanathan, Madison, WI (US); Scott Kuersten, Fitchburg, WI (US); Ken Doyle, Fitchburg, WI (US)

(73) Assignee: Epicentre Technologies Corporation, Madison, WI (US)

( * ) Notice: Subject to any disclaimer, the term of this patent is extended or adjusted under 35 U.S.C. 154(b) by 133 days.

(21) Appl. No.: 12/938,979

(22) Filed: Nov. 3, 2010

(65) Prior Publication Data
US 2011/0104785 A1 May 5, 2011

Related U.S. Application Data

(60) Provisional application No. 61/258,559, filed on Nov. 5, 2009.

(51) Int. Cl.
*C12Q 1/42* (2006.01)

(52) U.S. Cl.
USPC .......................................................... 435/21

(58) Field of Classification Search
None
See application file for complete search history.

(56) References Cited

U.S. PATENT DOCUMENTS

| 7,303,901 | B2 | 12/2007 | Hjorleifsdottir et al. | |
|---|---|---|---|---|
| 7,361,465 | B2 | 4/2008 | Murphy et al. | |
| 2005/0260640 | A1* | 11/2005 | Andersen et al. | 435/6 |
| 2006/0240451 | A1* | 10/2006 | Jendrisak et al. | 435/6 |
| 2008/0108804 | A1 | 5/2008 | Hayashizaki et al. | |
| 2009/0011422 | A1 | 1/2009 | Devor et al. | |

FOREIGN PATENT DOCUMENTS

| WO | 2009026148 | 2/2009 |
|---|---|---|
| WO | 2009091719 | 7/2009 |

OTHER PUBLICATIONS

Pfeffer et al. (2003) Current Protocols in Molecular Biology Supplement 64 26.4.1-26.4.18.*
T4 RNA Ligase 2 [online] [retrieved on Sep. 6, 2012] retrieved from http://www.neb.com/nebecomm/products/productm0239.asp].*
Yang et al. (1992) J. Biol. Chem. vol. 267 No. 12 pp. 8117-8122.*
Vigneault et al. (on line Aug. 2008) Nature methods vol. 5 No. 9 pp. 777-779.*
Yu et al. (2005) Science vol. 307 pp. 932-935.*
Ahel et al. (2006) Nature vol. 443 pp. 713-716.*
T4 RNA Ligase 1 [online] [retrieved on Sep. 6, 2012] retrieved from http://www.neb.com/nebecomm/products/productm0204.asp].*
Vigneault et al. (on line Aug. 2008) Supplementary material.*
Yu et al. (2005) Supplementary material.*
Ahel et al. (2006) The neurodegenerative disease protein aprataxin resolves abortive DNA ligation intermediates. Nature 443:713-717.
Amara and Vijaya, (1997) Specific polyadenylation and purification of total messenger RNA from *Escherichia coli*. Nucleic Acids Res. 25:3465-3470.
Carthew and Sontheimer, (2009) Origins and mechanisms of miRNAs and siRNAs. Cell 136: 642-655.
Cooper, Dl and Marzluff, Wf (1977) Polyadenylation of RNA in a cell-free system from mouse myeloma cells. J. Biol. Chem. 253:8375-8380.
Ebhardt, Ha et al. (2005) Extensive 3' modification of plant small RNAs is modulated by helper component-proteinase expression. Proc. Natl. Acad. Sci. USA 102:13398-13403.
England, Te et al. (1977) Dinucleoside pyrophosphates are substrates for T4-induced RNA ligase. Proc. Natl. Acad. Sci. USA 74:4839-4842.
Feng, Y and Cohen, S. (2000) Unpaired terminal nucleotides and 5' monophosphorylation govern 3' polyadenylation by *Escherichia coli* poly(A) polymerase I. Proc. Natl. Acad. Sci. USA 97:6415-6420.
Harbers, M. (2008) The current status of cDNA cloning. Genomics 91:232-242.
Hafner, M et al. (2008) Identification of microRNAs and other small regulatory RNAs using cDNA library sequencing. Methods 44:3-12.
Han, Es et al. (2006) RecJ exonuclease: substrates, products and interaction with SSB. Nucleic Acids Res. 34:1084-1091.
Ho, Ck and Shuman, S. (2002) Bacteriophage T4 RNA ligase 2 (gp24.1) exemplifies a family of RNA ligases found in all phylogenetic domains. Proc. Natl. Acad. Sci. USA 99:12709-12714.
Ho, Ck et al. (2004) Structure and mechanism of RNA ligase. Structure 12:327-339.
Kawano, M et al. (2010) Reduction of non-insert sequence reads by dimer eliminator LNA oligonucleotide for small RNA deep sequencing. BioTechniques 49:751-755.
Lovett, St and Kolodner, Rd. (1989) Identification and purification of a single-stranded-DNA-specific exonuclease encoded by the recJ gene of *Escherichia coli*. Proc. Natl. Acad. Sci. USA 86:2627-2631.
Maruyama, K and Sugano, S. (1994) Oligo-capping: a simple method to replace the cap structure of eukaryotic mRNAs with oligoribonucleotides. Gene 138: 171-174.
Nandakumar, J et al. (2004) RNA substrate specificity and structure-guided mutational analysis of bacteriophage T4 RNA ligase 2. J. Biol. Chem. 279:31337-31347.
Ponting, Cp et al. (2009) Evolution and functions of long noncoding RNAs. Cell 136: 629-641.
Saito, K et al. (2007) Pimet, the Drosophila homolog of HEN1, mediates 2'-O-methylation of Piwi-interacting RNAs at their 3' ends. Genes Dev. 21:1603-1608.
Sambrook, J et al. (1989) Molecular cloning: a laboratory manual (2nd ed). Cold Spring Harbor Laboratory Press, Cold Spring Harbor, NY. pp. 6-46.
Silverman, S. (2004) Practical and general synthesis of 5'-adenylated RNA (5'-AppRNA). RNA 10:731-746.
Steege, D. (2000) Emerging features of mRNA decay in bacteria. RNA 6:1079-1090.

(Continued)

*Primary Examiner* — Teresa E Strzelecka
*Assistant Examiner* — Suchira Pande
(74) *Attorney, Agent, or Firm* — Lisa de Berg; Illumina, Inc.

(57) ABSTRACT

The present innovation provides methods and kits that enable rapid and efficient dual end-tagging of RNA to prepare libraries for analysis by applications such as next-generation RNA sequencing, qPCR, microarray analysis, or cloning. The methods do not require time-consuming and inefficient gel-purification steps that are common to methods known in the art. In addition, the present invention provides methods and kits for rapid, high-throughput enzymatic preparation of 5'-activated, 3'-blocked DNA oligonucleotides from standard, single-stranded DNA oligonucleotides.

21 Claims, 8 Drawing Sheets

(56) References Cited

OTHER PUBLICATIONS

Takada, S et al. (2006) Mouse microRNA profiles determined with a new and sensitive cloning method. Nucleic Acids Res. 34:e115.

Vigneault, F et al. (2008) Efficient microRNA capture and bar-coding via enzymatic oligonucleotide adenylation. Nature Meth. 5:777-779.

Yang, Z et al. (2005) HEN1 recognizes 21-24 nt small RNA duplexes and deposits a methyl group onto the 2' OH of the 3' terminal nucleotide. Nucleic Acids Res. 34:667-675.

Yu, B et al. (2005) Methylation as a crucial step in plant microRNA biogenesis. Science 307:932-936.

Clepet, C. et al., "Improved full-length cDNA production based on RNA tagging by T4 DNA ligase", Nucleic Acids Res., vol. 32(1), e6, Jan. 2, 2004.

Vigneault, F. et al., "Efficient microRNA capture and bar-coding via enzymatic oligonucleotide adenylation", Nature Methods, Nature Publishing Group, vol. 5, No. 9, Sep. 1, 2008, 777-779.

\* cited by examiner

| Lane 1 | Lane 2 | Lane 3 | Lane 4 | Lane M |
|---|---|---|---|---|
| DNA Oligo SEQ ID NO.1 | Sample 1 (DNA Oligo SEQ ID NO.1 + TdT + ddATP) | Sample 2 (Sample 1 + T4 Polynucleotide Kinase + ATP) | Sample 3 (Sample 2 + CircLigase ssDNA Ligase) | DNA Marker |

| Lane 1 | Lane 2 | Lane 3 | Lane 4 | Lane 5 | Lane 6 | Lane 7 | Lane 8 | Lane 9 | Lane 10 |
|---|---|---|---|---|---|---|---|---|---|
| Oligo Marker | DNA Oligo SEQ ID No. 3 | 5'-p-DNA-X | 5'-App-DNA-X | 5'-p-DNA-X + RecJ | 5'-App-DNA-X + RecJ | 5'-p-DNA-X + TAP | 5'-App-DNA-X + TAP | 5'-p-DNA-X + TAP + RecJ | 5'-App-DNA-X + TAP + RecJ |

| Lane 1 | Lane 2 | Lane 3 | Lane 4 | Lane 5 | Lane 6 | Lane 7 | Lane 8 | Lane 9 | Lane 10 | Lane 11 | Lane 12 |
|---|---|---|---|---|---|---|---|---|---|---|---|
| RNA (SEQ ID NO. 4) | RNA + RNL2 (1-249) | 5'-App-DNA-X | 5'-App-DNA-X + RNL2 (1-249) | RNA + 5'-App-DNA-X + RNL2 (1-249) | [RNA + 5'-App-DNA-X + APex Alk Phos] + RNL2 (1-249) | #1 + TAP + RecJ | #2 + TAP + RecJ | #3 + TAP + RecJ | #4 + TAP + RecJ | #5 + TAP + RecJ | #6 + TAP + RecJ |

METHODS AND KITS FOR 3'-END-TAGGING OF RNA

The present application claims priority to U.S. provisional patent application Ser. No. 61/258,559 filed Nov. 5, 2009, the entire disclosure of which is herein incorporated by reference in its entirety.

FIELD OF THE INVENTION

The invention relates generally to the field of tagging of ribonucleic acid (RNA) molecules. In particular, it relates to improved methods for ligation-based tagging of RNA molecules, e.g., for identification and further characterization by applications such as next-generation RNA sequencing (RNA-Seq), quantitative reverse transcription-polymerase chain reaction (qRT-PCR), microarray analysis, or cloning.

BACKGROUND OF THE INVENTION

Messenger RNA (mRNA) has been the focus of RNA research since its discovery in the late 1950s. mRNA encodes proteins that are responsible for cell organization, structure, and function. mRNA constitutes from 1% to 5% of the total RNA within a cell. It was generally assumed that only the small percentage of human genomic deoxyribonucleic acid (DNA) that was transcribed into mRNA, ribosomal RNA, transfer RNA, and small nucleolar RNA was biologically significant; the vast, nontranscribed portion was considered "junk" DNA. Thus, the "central dogma" of molecular biology dictated that DNA was transcribed into RNA, which was, in the case of mRNA, in turn translated into protein.

Contrary to earlier assumptions underlying this central dogma of molecular biology, it is now known that most of the eukaryotic genome is transcribed, resulting in many RNAs that do not encode proteins. While the majority of this non-coding RNA (ncRNA) remains uncharacterized, it is becoming evident that most ncRNAs have significant biological function. Thus, RNA research has seen a major shift in focus in the past few years, from mRNA to ncRNA.

ncRNAs can be divided into two groups: long ncRNAs (greater than 200 nucleotides [nt]), and small ncRNAs (200 nt or smaller). Long ncRNAs are perhaps the least-understood type of ncRNA, and there is great interest in studying their roles in transcriptional regulation, epigenetic gene regulation, and disease pathways (Ponting, 2009). Small ncRNAs have already been the subject of intensive study. A subclass of small ncRNAs comprises RNAs that are 20-30 nt in length, and that have distinct regulatory functions; these include microRNA (miRNA), endogeneous small interfering RNA (siRNA), and piwi-interacting RNAs (piRNAs). These three types of small ncRNAs associate with distinct sets of effector proteins in order to exert their regulatory functions (reviewed in Carthew and Sontheimer, 2009).

The study of both coding and noncoding RNA has benefited greatly from analytical technologies such as quantitative reverse-transcription polymerase chain reaction (qRT-PCR), microarrays, and next-generation sequencing (RNA-Seq). These technologies typically require that the user: i) isolate the particular class of RNA molecules of interest from a total RNA preparation or directly from a biological sample; ii) take advantage of endogenous sequence "tags" when present, or introduce such tags when absent, at the 5' end, 3' end, or both; and iii) prepare complementary DNA (cDNA) from the tagged RNA.

The nature of the 5' ends of different classes of RNA molecules plays an important role in their biological structure and function. The chemical moieties on the 5' ends of RNA molecules influence their structure, stability, biochemical processing, transport, biological function and fate in a cell or organism. The chemical moieties commonly found at the 5' ends of different RNA classes include triphosphates, monophosphates, hydroxyls, and cap nucleotides. The particular chemical moiety on the 5' end provides important clues to the origin, processing, maturation, and stability of the RNA. Tagging the 5' end of RNA can be accomplished by selecting the RNA based on the type of 5' end, modifying the 5' end if necessary, and then ligating the desired tagging sequence contained in a DNA or RNA oligonucleotide (for example, see World Patent Application WO 2009/026148 A1; Maruyama, 1994).

The 3' ends of RNAs also undergo processing related to their origin, structure, and functional role within the cell. Almost all eukaryotic mRNAs have a polymeric stretch of adenine nucleotides at the 3' end, i.e., a "poly(A) tail"; this tail confers properties such as mRNA stability, enhances translation, and contributes to transport of the processed mRNA from the nucleus to the cytoplasm. In prokaryotes, a minority of mRNA transcripts are polyadenylated; the poly(A) tail is thought to be largely involved in degradation of these transcripts (Steege, 2000).

The presence of a poly(A) tail in a class of desired mRNAs facilitates their study by 3'-end-tagging, in which a tagging oligonucleotide containing a poly(dT) sequence is annealed to the poly(A) tail of the RNA. Using a reverse transcriptase enzyme, and the tagging oligonucleotide as a primer, first-strand complementary DNA (cDNA) can be synthesized. By including additional functional sequences at the 5' end of the tagging oligonucleotide, further analysis by a variety of methods is enabled, including expression microarrays, qRT-PCR, and RNA-Seq.

However, many types of RNA (including ncRNA) lack a poly(A) tail at the 3' end, making it difficult to characterize them using poly(dT)-containing tags. Therefore, methods have been developed in the art to introduce a 3'-poly(A) tail for those RNA molecules that lack such an endogenous sequence. Originally, crude nuclear extracts were used for in vitro polyadenylation of RNA, albeit with relatively low efficiency (Cooper and Marzluff, 1977). Subsequently, cloned and purified enzymes were used for in vitro polyadenylation. For example, poly(A) polymerase from yeast has been used to specifically polyadenylate E. coli polysomal mRNA (Amara and Vijaya, 1997). However, this method has some deficiencies. For example, using E. coli poly(A) polymerase, different RNAs may be polyadenylated to different extents, depending on the structure of their 5' and 3' ends (Feng and Cohen, 2000). Using standard conditions known in the art, the tailing reaction is not quantitative; thus, some RNA in a population would be lost to further analysis (U.S. Pat. No. 7,361,465 B2). Further, with small amounts of RNA (<100 ng), the added poly(A) tail is extremely long (up to 9 kb) (U.S. Pat. No. 7,361,465 B2).

U.S. Pat. No. 7,361,465 B2 provides methods and compositions for tailing nonpolyadenylated RNA molecules, including miRNA, siRNA, tRNA, rRNA, synthetic RNA, or nonpolyadenylated mRNA. The inventors describe improvements in both efficiency of polyadenylation, and in reducing the length of the poly(A) tail. The optimized reaction conditions described by the inventors limit the length of the poly(A) tail to no more than 500 nt.

However, homopolymeric tails can be problematic for applications such as next-generation sequencing, when the poly(A) tail sequence introduces additional nucleotides between the sequencing primer and the sequence of the desired RNA. It is also desirable to precisely control the length of the poly(A) tail so that the same number of A nucleotides is added each time; i.e., the reaction is reproducible.

Further, it is known that poly(A) polymerase is inefficient in polyadenylating RNA molecules that have a 2'-O-methyl group on the 3'-terminal ribose (Ebhardt, 2005; Yang, 2005). Such modified RNAs include plant miRNAs and siRNAs (Yu, 2005; Yang, 2005) and some higher eukaryotic piRNAs (Saito, 2007). To address these shortcomings of polyadenylation, methods have been developed to tag the 3' end of RNA molecules using modified oligonucleotides, taking advantage of the properties of different types of RNA ligase enzymes.

RNA Ligase 1 from bacteriophage T4-infected *E. coli* (T4 RNA Ligase 1) catalyzes the adenosine triphosphate (ATP)-dependent formation of a 3' to 5' phosphodiester bond between an RNA molecule with a 3'-hydroxyl group (the acceptor molecule) and another molecule bearing a 5'-phosphoryl group (the donor molecule). The reaction occurs in three steps, involving covalent intermediates (Silverman, 2004; England 1977):

i) T4 RNA Ligase 1 reacts with ATP to form a covalent enzyme-ATP intermediate ("adenylated enzyme"), with the release of pyrophosphate.

ii) The adenyl group is transferred from the adenylated enzyme to the 5'-phosphoryl end of a RNA molecule, to form a 5',5'-phosphoanhydride bond (5'-App-RNA) with the elimination of adenosine monophosphate (AMP).

iii) The 5'-App-RNA donor reacts with the 3'-hydroxyl group of another acceptor RNA molecule, in the absence of ATP, to form a standard 3' to 5' phosphodiester bond between the acceptor and donor RNA molecules.

A 5'-adenylated DNA molecule may also be used as the donor molecule in step (iii) above. This approach has proven useful in 3'-ligation-tagging of RNA molecules. In one example of this method, a 5'-adenylated donor oligonucleotide (5'-App-DNA) is ligated to the 3' end of a miRNA acceptor using T4 RNA Ligase 1 in the absence of ATP (Ebhardt, 2005). In another example of this method, the 5'-adenylated donor oligonucleotide additionally contains a blocking group at its 3' end (5'-App-DNA-X), thereby preventing self-ligation of the donor oligonucleotide (Hafner, 2008); the reaction is catalyzed by T4 RNA Ligase 2.

Such 5'-adenylated, 3'-blocked oligonucleotides are available commercially (US Patent Application 2009/0011422 A1; Vigneault, 2008). However, commercial synthesis of such 5'- and 3'-modified oligonucleotides can be inefficient and expensive compared to standard (unmodified) oligonucleotides, especially when many oligonucleotides are required for applications such as preparing barcoded libraries for RNA-Seq (Vigneault, 2008).

Enzymatic methods are known in the art for 5'-adenylating oligonucleotides (e.g., see Vigneault, 2008). Since these methods still rely on the chemical addition of a 3'-blocking group to the DNA oligonucleotide during its synthesis, they also incur increased costs compared to synthesizing an unmodified oligonucleotide. In addition, the methods require gel-purification of the adenylated oligonucleotide, which is time-consuming and tedious, especially when a large number of adenylated oligonucleotides are required to be prepared, or when the reaction needs to be scaled up or performed in a high-throughput format (i.e., simultaneously with a large number of samples). Needed in the art is a simple, single-tube enzymatic method for 5' adenylating and 3' blocking of standard oligonucleotides. Such a method is desirable because it can be easily incorporated into a high-throughput workflow, for example, 3' tagging of RNA with barcoded oligonucleotides for RNA-Seq.

In methods for 3'-end-tagging of RNA using 5'-adenylated DNA oligonucleotides, a large molar excess of the donor oligonucleotide is often used to increase the efficiency of the ligation. After termination of the ligation reaction, this excess of donor oligonucleotide must be removed before proceeding with subsequent enzymatic manipulation of the 3'-end-tagged RNA. The excess adaptor is problematic because, if not removed, it can lead to the formation of adaptor-dimer products that contribute to high background during sequencing. The methods known in the art use gel purification to remove excess donor oligonucleotide. This technique involves separation of the reaction products by polyacrylamide gel electrophoresis, excision of a gel slice containing the desired product, elution of the desired product from the gel slice by mechanical agitation in a suitable buffered solution, and ethanol precipitation to concentrate and purify the desired product (e.g., see Vigneault, 2008; Hafner, 2008). It is sometimes possible to skip the gel purification before proceeding to 5'-adaptor ligation; however, gel purification is still required before proceeding to applications such as cloning or next-generation sequencing (Vigneault, 2008). A modified purification method has been described (US Patent Application 2009/0011422 A1) that also uses gel purification.

Recently, a method has been described to remove adaptor-dimer products by using a locked nucleic acid (LNA) that is complementary to the adaptor-dimer products (Kawano, 2010, BioTechniques 49:751-755). This LNA binds to, and prevents reverse transcription from, adaptor dimers. Thus, during sequencing of small-RNA libraries prepared by this method, background due to non-insert sequence reads is reduced. However, this method does not attempt to reduce the formation of adaptor dimers, which is due to the presence of excess donor oligonucleotide. An alternative method for preparing dual-tagged RNA libraries has been described, using sequential addition of adaptors to RNA, followed by reverse transcription and PCR, to generate a double-stranded (ds) cDNA library for sequencing (World Patent Application WO 2009/091719 A1). Although some embodiments of the methods in World Patent Application WO 2009/091719 A1 do not specifically mention a requirement for gel purification, the exemplary embodiments show that there is a substantial amount of undesired byproducts generated in the reaction. These byproducts need to be removed by either gel purification or high-performance liquid chromatography before sequencing the cDNA library (for example, see FIG. 3 in World Patent Application WO 2009/091719 A1).

Gel purification is a time-consuming process, and the efficiency of recovery can vary greatly (Sambrook, 1989). Further, the procedure subjects the RNA-DNA ligation product to increased risk of degradation. Thus, needed in the art are methods and kits for rapid and highly efficient removal of excess donor oligonucleotide from a ligation reaction, e.g., prior to subsequent enzymatic manipulation of the ligation reaction products, thereby preventing formation of adaptor dimers that can cause high background in RNA-Seq. Also needed in the art are methods and kits that provide rapid and efficient 3' tagging of nonpolyadenylated RNA for applications such as cloning, microarray analysis and next-generation sequencing, without incurring potential loss of sample through multiple gel-purification steps.

SUMMARY OF THE INVENTION

The present invention provides a rapid and efficient enzymatic method for removal of excess activated DNA oligonucleotide from a sample following a bimolecular ligation reaction. This method increases the sensitivity of detection of the bimolecular ligation product by techniques such as RNA-Seq. Unlike methods known in the art, the present invention does not employ tedious and inefficient gel purification procedures or, in a RNA-Seq workflow, merely inactivate already formed adaptor dimers by using LNA; thus, the present invention can be used with substantially less input RNA compared to other methods known in the art. The present invention also provides kits for preparing end tagged and dual end-tagged RNA or ds cDNA libraries, suitable for applications such as next-generation sequencing, qPCR, microarray analysis, or cloning.

The present invention additionally provides novel methods for enzymatic preparation of 5'-activated, 3'-blocked DNA oligonucleotides from any standard DNA oligonucleotide (e.g., one that is prepared by chemical or enzymatic synthesis, or by other means, and that has been prepared or treated so as to have hydroxyl groups on the 5' and 3' termini). The present invention also provides kits for preparing such 5'-activated, 3'-blocked oligonucleotides from standard DNA oligonucleotides in a rapid, high-throughput format.

DETAILED DESCRIPTION OF THE INVENTION

Figure 1:
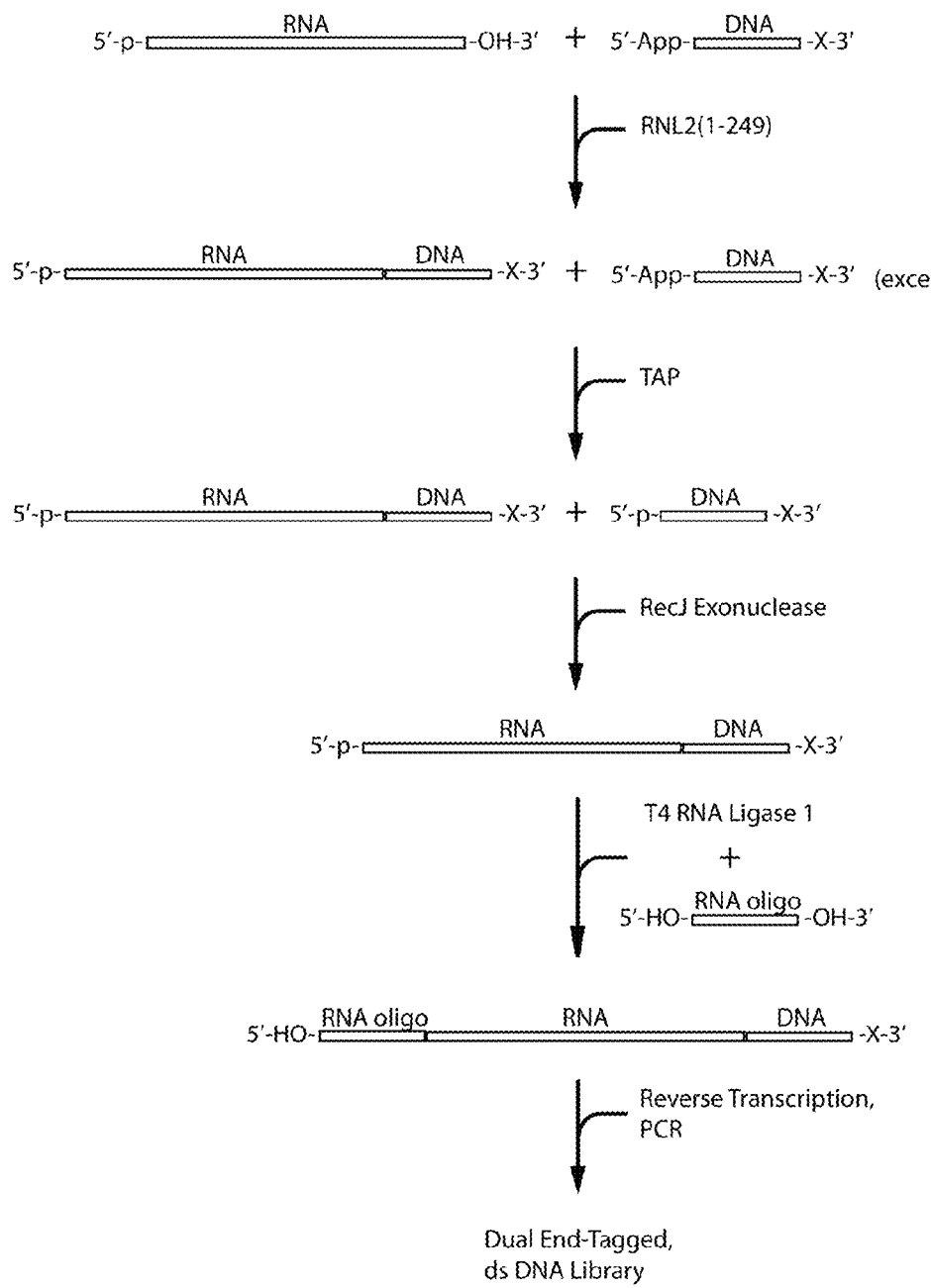
FIG. 1 is an illustration of an exemplary embodiment of the described methods for preparing an end-tagged ds cDNA library from RNA.

The present invention provides methods and kits for enzymatic removal of excess 5'-adenylated donor DNA oligonucleotide from a sample following a bimolecular ligation reaction. Advantages of the present invention compared to the prior art include a rapid, enzymatic process that does not require gel purification to remove the excess activated donor DNA oligonucleotide, and that enables the ligation products to be directly used in further enzymatic methods, e.g., to produce 5'- and 3'-end-tagged RNA libraries for applications including next-generation sequencing, qRT-PCR, microarray expression analysis, or cloning.

In a preferred embodiment, the present invention provides a novel method for removal of excess 5'-adenylated, 3'-blocked DNA oligonucleotide following a bimolecular ligation reaction between RNA that has a free 3'-hydroxyl end and the 5'-adenylated, 3'-blocked DNA oligonucleotide. In a preferred aspect of this embodiment, the 3'-blocking group of the DNA oligonucleotide is a dideoxynucleotide. Dideoxynucleotides lack hydroxyl groups on both the 2' and 3' positions of the ribose sugar moiety; therefore, they cannot form a 3' to 5' phosphodiester bond. Those skilled in the art will appreciate that other 3' blocking groups may also be employed; for example, an inverted deoxycytidine (Takada, 2006), or an amino spacer.

By including a blocking group on the 3' end of the activated donor DNA oligonucleotide, intramolecular ligation or bimolecular ligation of one molecule of activated donor DNA oligonucleotide to another is essentially eliminated, thereby avoiding the formation of undesired DNA-DNA ligation products (e.g., dimers, concatamers, circles, etc.). Further, the 3'-blocking group is useful if the RNA-DNA molecule is subsequently 5'-end-tagged by ligation of a second oligonucleotide that has a 3'-hydroxyl group. In such a reaction, the 3'-blocking group on the RNA-DNA molecule ensures that the second oligonucleotide is ligated exclusively to the 5' end of the RNA-DNA molecule.

Oligonucleotides of many different sequences and lengths can be employed as the DNA donor molecule in the bimolecular ligation reaction; however, in preferred embodiments, the features of the oligonucleotides used in the methods of the present invention are the presence of: i) a 5'-adenylated nucleotide at the 5' end, and ii) a blocking group at the 3' end.

In some embodiments of the present invention, the bimolecular ligation between the RNA acceptor and 5'-adenylated DNA oligonucleotide donor is catalyzed by T4 RNA Ligase 1, T4 RNA Ligase 2, bacteriophage TS2126 ligase (U.S. Pat. No. 7,303,901), or CircLigase ssDNA Ligase. In preferred aspects of these embodiments, the reaction is catalyzed by truncated T4 RNA Ligase 2.

Truncated T4 RNA Ligase 2 specifically ligates the 5'-adenylated end of a DNA donor oligonucleotide to the 3'-hydroxyl end of an acceptor RNA in the absence of ATP (Ho and Shuman, 2002; Nandakumar, 2004). In preferred embodiments, the 5'-adenylated DNA oligonucleotide is present in molar excess so as to favor the desired ligation reaction. Unlike the full-length enzyme, truncated T4 RNA Ligase 2 has a defect in the ability to transfer the adenyl group to the 5' end of RNA; therefore, it cannot efficiently ligate the phosphorylated 5' end of one RNA molecule to the 3' end of the same or another RNA molecule (Nandakumar, 2004). Thus, formation of undesired RNA-RNA ligation products is reduced.

In a preferred embodiment of the present invention, the ligation reaction products, which include the desired RNA-DNA molecule as well as the excess 5'-adenylated DNA oligonucleotide, are treated to de-adenylate residual 5' adenylated DNA oligonucleotide.

De-adenylation is not limited to any particular method. In some preferred embodiments, the ligation reaction products are incubated with Tobacco Acid Pyrophosphatase (TAP). This enzyme is available commercially from EPICENTRE, and hydrolyzes the phosphoric acid anhydride bonds in the triphosphate bridge of the cap structure found in most eukaryotic mRNA or of the 5'-triphosphate found in primary RNA, generating a 5'-monophosphorylated terminus on the RNA molecule. The inventors have discovered that TAP can also deadenylate 5'-adenylated DNA, generating a 5'-monophosphorylated DNA molecule.

In other embodiments, the ligation reaction products are incubated with Yeast 5' Deadenylase, which converts the 5'-adenylated DNA oligonucleotide to a 5'-monophosphorylated DNA oligonucleotide (see Ahel, 2006).

In some preferred embodiments of the present invention, after the excess 5'-adenylated DNA oligonucleotide is converted to a 5'-monophosphorylated DNA oligonucleotide, e.g., by TAP, the reaction is treated to remove or degrade the DNA oligonucleotide. For example, in some preferred embodiments, the reaction mixture is incubated directly with an exonuclease, e.g., RecJ Exonuclease. This enzyme is available commercially from EPICENTRE. *E. coli* RecJ Exonuclease is a $Mg^{2+}$-dependent 5' to 3' single-stranded DNA (ssDNA)-specific exonuclease (Lovett and Kolodner, 1989; Han, 2006). Therefore, it degrades the excess 5'-monophosphorylated DNA oligonucleotide but is unable to degrade the RNA-DNA ligation product; the RNA portion of this molecule essentially acts as a blocking group against the 5' to 3' ssDNA exonuclease activity of RecJ Exonuclease. The inventors have discovered that RecJ Exonuclease does not degrade 5'-adenylated DNA, but does degrade the DNA oligonucleotides after the adenyl group is removed (e.g., by the action of TAP or Yeast 5'-Deadenylase). Those skilled in the art will appreciate that other DNA 5' to 3' exonucleases that digest ssDNA and that do not have RNA-dependent endonuclease or exonuclease activity can also be used instead of RecJ Exonuclease, (e.g., Lambda Exonuclease, available from EPICENTRE).

In some embodiments, the present invention improves upon methods known in the art for 3'-end-tagging of RNAs that are not polyadenylated, (e.g., for the purpose of next-generation sequencing). RNAs that are not polyadenylated include most eukaryotic ncRNAs (such as miRNAs, endogeneous siRNAs, shRNAs and piRNAs), most prokaryotic RNAs, and fragmented mRNAs such as may be produced from degraded mRNA samples or by chemical or mechanical manipulation of longer RNAs. In other embodiments, the present invention also improves upon methods known in the art for 3'-end-tagging of RNAs that have a 2'-O-methyl group on their 3'-terminal nucleotide. Such RNAs include the majority of plant miRNAs and siRNAs, and some eukaryotic piRNAs. Thus, the present invention reduces the time and effort required to prepare 3'-end-tagged RNA from any RNA by eliminating the necessity for gel purification steps that are common to methods known in the art. Further, since gel purification steps are associated with loss of product, the method of the present invention requires substantially less input RNA compared to methods known in the art. In some embodiments, the methods of the present invention may be used to add a tag at the 3' end of a poly(A) tail, e.g., of an mRNA.

Those skilled in the art will appreciate that the 3'-end-tagged RNA obtained by performing the methods of the present invention can be readily used to prepare 5'- and 3'-end-tagged cDNA libraries for a variety of applications. For example, the 3'-end-tagged RNA can be incubated with a RNA oligonucleotide containing a tagging sequence that has a 3'-hydroxyl terminus, and RNA Ligase. The product of this second ligation reaction is a library of RNA molecules that are tagged with defined sequences on both the 5' and 3' ends. Further, this RNA library can be incubated with a primer that contains a sequence complementary to the 3'-tagging sequence, a reverse transcriptase enzyme, deoxyribonucleotide triphosphates (dNTPs), and under appropriate conditions wherein first-strand cDNA is synthesized that is complementary to the tagged RNA. This first-strand cDNA can be converted to ds cDNA by PCR amplification, resulting in a cDNA library that is tagged at both the 5' and 3' ends. Thus, the 3'-end-tagged RNA produced by the methods of the present invention can be converted to a 5'- and 3'-end tagged, ds cDNA library for further analysis (FIG. 1).

In preferred embodiments of the present invention, the 5'-adenylated 3'-blocked DNA donor oligonucleotide includes an adaptor sequence for next-generation sequencing platforms including 454 FLX™ or Titanium (Roche), Solexa® GAI or GAII (Illumina), or SOLiD™ (Applied Biosystems). By including a second adaptor sequence in a 5'-tagging RNA oligonucleotide, and converting the RNA to a 5'- and 3'-end-tagged, ds cDNA library with the appropriate PCR primers, the library can be used as template for next-generation sequencing on the platform of choice. Thus, the methods of the present invention enable the sequences of unknown RNA molecules to be determined by RNA-Seq. Further, the relative amounts (expression levels) of a targeted RNA in different cell or tissue types, or in cells from normal or diseased tissues, can be compared by RNA-Seq. Thus, the methods of the present invention can be used, for example, to study specific pathways in which targeted RNAs are involved in the response of cells to environmental or chemical stress, or those involved in development of cancer or other disease states.

In other embodiments, the 5'-adenylated, 3'-blocked DNA donor oligonucleotide contains a restriction endonuclease site adjacent to or in place of the next-generation sequencing adaptor sequence. By including a second restriction endonuclease site in a 5'-tagging RNA oligonucleotide, and converting the RNA to a 5'- and 3'-end-tagged, ds cDNA library, the cDNA can be cloned into a suitable vector (such as a plasmid vector, bacteriophage lambda vector, or fosmid vector [e.g., EPICENTRE's CopyControl™ Cloning-Ready Fosmid Vectors]) for further analysis. The second restriction endonuclease site can be the same as, or different from, the first restriction endonuclease site. Further, the restriction endonuclease site can be chosen such that it is likely to occur very rarely or not at all in the sequence of the cDNA (e.g., NotI restriction endonuclease). Thus, the methods of the present invention can be used to prepare a cloned cDNA library that represents all the RNA molecules of a desired type from a particular cell, tissue type, or organism. For example, the methods of the present invention can be used to prepare a cloned library of small ncRNA for functional studies that supplement the data obtained by sequencing, or for cloning long ncRNAs to study the regulation of RNA maturation processes (Haber, 2008).

In still other embodiments, the 5'-adenylated, 3'-blocked DNA donor oligonucleotide contains a RNA polymerase promoter sequence. By preparing ds cDNA from the 3'-tagged RNA produced by performing the methods of the present invention, the RNA polymerase promoter sequence is incorporated in a location and orientation such that in vitro transcription driven from the promoter sequence will produce an antisense RNA transcript, with respect to the original RNA from which the ds cDNA was produced. Thus, many antisense copies of the original (sense) RNA molecule are produced by in vitro transcription, and the RNA is said to be "amplified." Kits are available commercially that produce very high yields of RNA by in vitro transcription of linear ds DNA, such as cDNA, using bacteriophage SP6, T3, or T7 RNA Polymerase under optimized conditions (such as the AmpliScribe™ High-Yield and AmpliScribe Flash™ InVitro Transcription Kits from EPICENTRE). Amplification of RNA is highly desirable when working with very small amounts of RNA obtained from biological samples such as needle biopsies of tumors, limited numbers of cells (e.g., stem cells), or a single cell obtained by laser-capture microdissection techniques. The amplified antisense RNA can then be used for expression analysis by a variety of techniques, including qRT-PCR and microarrays. Thus, the methods of the present invention can be used to prepare amplified RNA from very small quantities of starting RNA obtained from biological samples.

One embodiment of the present invention is a kit comprising one or more of the following components to prepare RNA tagged at both the 5' and 3' ends: one or more 5'-adenylated, 3'-blocked DNA oligonucleotides and one or more 5'- and 3'-hydroxyl RNA oligonucleotides (e.g., with tagging sequences comprising a next-generation sequencing adaptor, a RNA polymerase promoter, or a restriction endonuclease site); an RNA ligase or RNA ligases (e.g., T4 RNA Ligase, T4 RNA Ligase 2, or truncated T4 RNA Ligase 2) and ligation buffers; a pyrophosphatase or deadenylase enzyme (e.g., TAP or Yeast 5'-Deadenylase); a 5' to 3' ssDNA exonuclease (e.g., RecJ Exonuclease or Lambda Exonuclease); and reaction buffers. In some embodiments, a kit of the present invention provides all of these components.

Another embodiment of the present invention is a kit to prepare 5'- and 3'-end-tagged, ds cDNA, comprising one or more of the components listed above, and additionally comprising: a first-strand cDNA synthesis primer or primers (e.g., a primer complementary to the 3'-end-tagging oligonucleotide); a reverse transcriptase enzyme (e.g., AMV or MML Reverse Transcriptase (EPICENTRE), MonsterScript™ Reverse Transcriptase (EPICENTRE), SuperScript™ II or II Reverse Transcriptase (Invitrogen)); dNTPs; a PCR primer or primers; and reaction buffers. In some embodiments, the kits of the present invention comprise a ribonuclease inhibitor.

The present invention also provides methods and kits for preparation of a 5'-activated, 3'-blocked DNA oligonucleotide from a standard DNA oligonucleotide that has 5'- and 3'-hydroxyl termini. In some embodiments, the methods and kits provided are for the enzymatic preparation of a 5'-activated, 3'-blocked DNA oligonucleotide. A preferred embodiment comprises three sequential enzymatic reaction steps that are performed in the same reaction vessel.

By way of example and not limitation to any particular procedure, in some embodiments, a 5'-adenylated, 3'-blocked DNA oligonucleotide is produced according to the following procedure:

(A) A dideoxynucleotide is added to the 3' terminus of a DNA oligonucleotide by Terminal Deoxynucleotidyl Transferase (commercially available from Promega Corp and other sources), thereby producing a 3'-blocked DNA oligonucleotide. The reaction is performed in a buffered solution that comprises $Mg^{2+}$, KCl, and DTT (e.g., "CircLigase Buffer," EPICENTRE).

(B) The sample from step (A) is diluted with Nuclease-Free Water (available commercially from EPICENTRE or other sources, or produced by methods known in the art), and concentrations of the other components are adjusted for optimal activity by adding concentrated reaction buffer (e.g., CircLigase Buffer). Next, ATP is added, followed by a kinase enzyme. In a preferred aspect of this embodiment, the kinase enzyme comprises T4 Polynucleotide Kinase (commercially available from EPICENTRE or other sources). Under these conditions and after incubation for sufficient time, the 3'-blocked DNA oligonucleotide is phosphorylated at its 5' terminus to produce a 5'-phosphorylated, 3'-blocked DNA oligonucleotide.

(C) The sample from step (B) is diluted with Nuclease-Free Water, and concentrations of the other components are adjusted for optimal activity by adding concentrated reaction buffer (e.g., CircLigase Buffer). Next, ATP is added, followed by a single-strand ligase. In some aspects of this embodiment, the single-strand ligase comprises T4 RNA Ligase or T4 RNA Ligase 2, which have optimal activity at temperatures between 25° C. to 37° C. Some oligonucleotides may contain regions that are partially self-complementary, and they may form short double-stranded stretches in solution; these structures may not denature or "melt" at 37° C. and may inhibit efficient adenylation of the oligonucleotide if they are located at or near the 5' end. Therefore, it is desirable to perform the adenylation reaction at higher temperatures, which would melt local double-stranded regions of the oligonucleotide. Thus, in a preferred aspect of this embodiment, the single-strand ligase comprises bacteriophage TS2126 Ligase or CircLigase ssDNA Ligase (EPICENTRE), which have optimal activity at 60° C. Under these conditions and after sufficient time, the 5'-phosphorylated, 3'-blocked DNA oligonucleotide is converted to 5'-adenylated, 3'-blocked DNA oligonucleotide.

Following the reactions described above, the nucleic acid can be purified by methods known in the art, e.g., by phenol and chloroform extractions, followed by gel-filtration spin-column chromatography.

One embodiment of the present invention is a kit comprising one or more of the following components: a dideoxynucleotide triphosphate (ddNTP); ATP; Terminal Deoxynucleotidyl Transferase; a kinase (e.g., T4 Polynucleotide Kinase, EPICENTRE); a single-strand ligase enzyme (e.g., CircLigase ssDNA Ligase [EPICENTRE]); and reaction buffers. In some embodiments, a kit of the present invention provides all of these components.

Embodiments of the method disclosed in the present invention improve upon methods known in the art for preparing 5'-adenylated, 3-blocked oligonucleotides by avoiding synthetic chemical steps that are costly and that require inefficient and tedious gel-purification. Additionally, the method disclosed in the present invention is easy to perform in a high-throughput reaction format, such as in 96-well or 384-well microtiter plates and/or when using automated equipment. Thus, the methods provide rapid, efficient, and high-throughput preparation of oligonucleotides suitable for applications such as barcoding RNA samples for RNA-Seq.

Definitions

The present invention will be understood and interpreted based on terms as defined below.

The terms "comprising," "containing," "having," and "including" are to be construed as "including, but not limited to" unless otherwise noted. The terms "a," "an," and "the" and similar referents in the context of describing the invention and, specifically, in the context of the appended claims, are to be construed to cover both the singular and the plural unless otherwise noted. The use of any and all examples or exemplary language ("for example," "e.g.," "such as") is intended merely to illustrate aspects or embodiments of the invention, and is not to be construed as limiting the scope thereof, unless otherwise claimed.

As used herein, "noncoding RNA" or "ncRNA" means RNA found in or isolated from a biological sample that is not known to be translated into protein.

The terms "sample" and "biological sample" are used in their broadest sense and encompass samples or specimens obtained from any source, including biological and environmental sources. As used herein, the term "sample" when used to refer to biological samples obtained from organisms, includes bodily fluids, isolated cells, fixed cells, cell lysates and the like. The organisms include bacteria, viruses, fungi, plants, animals, and humans However, these examples are not to be construed as limiting the types of samples or organisms that find use with the present invention.

As used herein, the term "incubating" and variants thereof mean contacting one or more components of a reaction with another component or components, under conditions and for sufficient time such that a desired reaction product is formed.

As used herein, a "nucleoside" refers to a molecule consisting of a guanine (G), adenine (A), thymine (T), uridine (U), or cytidine (C) base covalently linked to a pentose sugar, whereas "nucleotide" or "mononucleotide" refers to a nucleoside phosphorylated at one of the hydroxyl groups of the pentose sugar.

Linear nucleic acid molecules are said to have a "5' terminus" (5' end) and a "3' terminus" (3' end) because, except with respect to adenylation (as described elsewhere herein), mononucleotides are joined in one direction via a phosphodiester linkage to make oligonucleotides, in a manner such that a phosphate on the 5' carbon of one mononucleotide sugar moiety is joined to an oxygen on the 3' carbon of the sugar moiety of its neighboring mononucleotide. Therefore, an end of an oligonucleotide is referred to as the "5' end" if its 5' phosphate is not linked to the oxygen of the 3' carbon of a mononucleotide sugar moiety, and as the "3' end" if its 3' oxygen is not linked to a 5' phosphate of a subsequent mononucleotide sugar moiety. A terminal nucleotide, as used herein, is the nucleotide at the end position of the 3' or 5' terminus.

As used herein, a "nucleic acid" or a "polynucleotide" is a covalently linked sequence of nucleotides in which the 3' position of the sugar moiety of one nucleotide is joined by a phosphodiester bond to the 5' position of the sugar moiety of the next nucleotide (i.e., a 3' to 5' phosphodiester bond), and in which the nucleotides are linked in specific sequence; i.e., a linear order of nucleotides. As used herein, an "oligonucleotide" is a short polynucleotide or a portion of a polynucleotide. For example, but without limitation, an oligonucleotide may be between 10-60 nucleotides in length. In some embodiments, the oligonucleotide consists of or comprises 2'-deoxyribonucleotides (DNA). In some embodiments, the oligonucleotide consists of or comprises ribonucleotides (RNA).

An "acceptor oligonucleotide," as used herein, means an oligonucleotide that has a 3'-hydroxyl group that is capable of being ligated to the 5' end of a RNA molecule that has a 5'-phosphate group by the action of a RNA ligase, wherein the RNA that has a 5'-phosphate group is referred to as the "donor." An acceptor oligonucleotide that consists of ribonucleotides is referred to herein as a "RNA acceptor oligonucleotide" or a "RNA acceptor."

As used herein, an "activated" oligonucleotide is a DNA or RNA oligonucleotide that has a chemical moiety on its 5' terminus that enables the oligonucleotide to participate as a donor molecule in a bimolecular ligation reaction. Examples of chemical moieties for activation include a 5'-phosphoryl or 5'-adenyl group.

Figure 2:
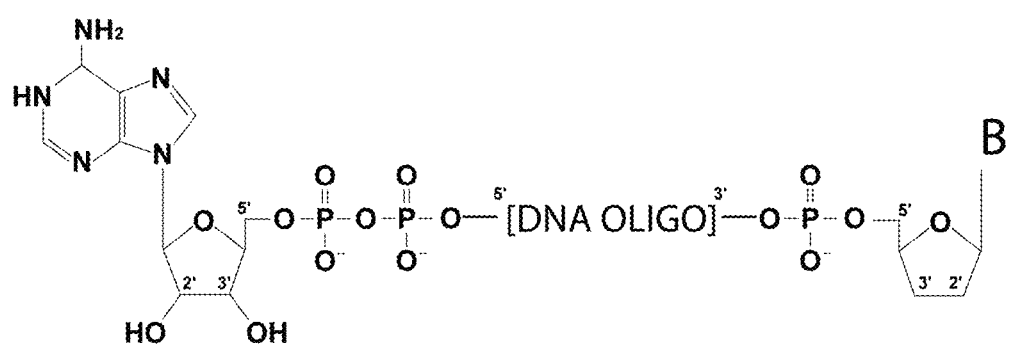
FIG. 2 is an illustration of a 5'-adenylated, 3'-blocked DNA oligonucleotide. "B" denotes the base attached to the ribose ring at the 1' position.

As used herein, a "5-adenylated" oligonucleotide is a DNA or RNA oligonucleotide that has, at its 5' terminus, an adenyl group covalently joined to the first nucleotide by a 5',5'-phosphoanhydride bond (see FIG. 2).

As used herein, a "3'-blocked" oligonucleotide is a DNA or RNA oligonucleotide in which the 3'-terminal nucleotide contains a modified deoxyribose (for DNA) or ribose (for RNA) sugar such that the 3'-hydroxyl group is unavailable for further extension of the oligonucleotide by 3' to 5' phosphodiester bond formation.

As used herein, the term "bimolecular ligation" means an enzymatic reaction in which a polynucleotide with a 5'-activated nucleotide (e.g., a 5'-phosphoryl or 5'-adenyl group), called the "donor" or "donor molecule" or "donor oligonucleotide," is covalently joined to another polynucleotide with a 3'-hydroxyl nucleotide, called the "acceptor" or "acceptor molecule or "acceptor oligonucleotide." In some preferred embodiments, wherein the polynucleotide with a 5'-activated nucleotide consists of DNA, the polynucleotide is a "DNA donor" or "DNA donor molecule" or "DNA donor oligonucleotide"; and wherein the polynucleotide with a 3'-hydroxyl group consists of RNA, the polynucleotide is a "RNA acceptor" or "RNA acceptor molecule" or "RNA acceptor oligonucleotide".

As used herein, a "tag" is a sequence of DNA or RNA, called the "tag sequence," that permits identification, recognition, and/or molecular or biochemical manipulation of the DNA to which the tag is joined or attached. For example, a tag may provide a site for annealing a primer (i.e., a "priming site") for DNA sequencing or nucleic acid amplification reaction. The process of joining the tag to the DNA or RNA molecule is sometimes referred to herein as "tagging" and the DNA or RNA that undergoes tagging is referred to as "tagged" (e.g., "tagged DNA" or "tagged RNA"). The tag can comprise one or more "tag sequences" or "tag portions," which mean herein a portion of the tag that contains a sequence for a desired intended purpose or application. The names and descriptions of different tag portions used herein are for convenience, such as to make it easier to understand and discuss the intended purposes and applications of the different portions of the tag in different embodiments. However, these names and descriptions are not intended to limit the use or applications of the tag or of any of its tag portions in any way. Thus, any particular tag or tag portion can be used for any purpose in addition to, or in place of the intended or primary purpose or application. A "sequencing tag" means a tag portion that facilitates sequencing of the RNA or DNA to which the tag is joined (e.g., to provide a priming site for sequencing by synthesis, or to provide annealing sites for sequencing by ligation, or to provide annealing sites for sequencing by hybridization). A "restriction site tag" means a tag portion that contains a sequence for the purpose of facilitating cleavage using a restriction endonuclease. A "promoter sequence tag" or a "promoter tag" means a tag portion that contains a sequence suitable for initiating transcription by a suitable RNA polymerase, for example, T3 RNA Polymerase, T7 RNA Polymerase, or SP6 RNA Polymerase. One tag portion can comprise or provide the functions or purposes or applications of two or more other tag portions (e.g., a sequencing tag portion can comprise both a sequencing portion and a restriction site portion). Still further, the tag need not be described in terms of one or more different portions in order to be used for any particular purpose, application, or function.

As used herein, the term "enzyme" refers to protein molecules or protein molecule aggregates that are responsible for catalyzing chemical and biological reactions. In general, a method or kit of the invention is not limited to use of a particular enzyme from a particular source. Rather, a method or kit of the present invention comprises any enzyme from any source that has an equivalent enzymatic activity to the particular enzyme disclosed herein with respect to the particular method or kit.

As used herein, the terms "nuclease" mean an enzyme that catalyzes the hydrolysis of phosphodiester bonds between the nucleotide subunits of a DNA or RNA molecule. DNA nucleases can be broadly divided into two groups: DNA exonucleases, which cleave nucleotides one at a time from the end of a DNA polynucleotide chain, and DNA endonucleases, which cleave the phosphodiester bond within a DNA polynucleotide chain.

As used herein, a "nucleic acid pyrophosphatase" or "pyrophosphatase" means an enzyme that cleaves pyrophosphate bonds of the triphosphate bridge of $m^7G$-capped RNA or of the 5' triphosphate in primary RNA to generate RNA that has a 5' monophosphate. The nucleic acid pyrophosphatase can be Tobacco Acid Pyrophosphatase ("TAP") or it can be any other enzyme that has similar activity in the method.

As used herein, a "nucleic acid deadenylase" or "deadenylase" is an enzyme the catalyzes the hydrolysis of AMP from the 5' end of adenylated DNA or RNA, leaving a 5'-phosphorylated DNA or RNA.

As used herein, "RNA ligase" means an enzyme that is capable of catalyzing the joining or ligating of an RNA acceptor molecule, which has a hydroxyl group on its 3' terminus, to a RNA or DNA donor molecule, which has a 5' phosphate group on its 5' terminus. The invention is not limited with respect to the RNA ligase, and any RNA ligase from any source can be used in an embodiment of the methods and kits of the present invention. For example, in some embodiments, the RNA ligase is a polypeptide (gp63) encoded by bacteriophage T4 gene 63; this enzyme, which is commonly referred to simply as "T4 RNA Ligase," is more correctly now called "T4 RNA Ligase 1" since a second RNA ligase (gp24.1) that is encoded by bacteriophage T4 gene 24.1 is known, which is now called "T4 RNA Ligase 2" (Ho and Shuman, 2002). Unless otherwise stated, when "T4 RNA Ligase" is used in the present specification, we mean "T4 RNA Ligase 1." Also as defined herein, "truncated T4 RNA Ligase 2" refers to the T4 RNA Ligase 2 mutant containing the N-terminal residues 1-249, also known as Rnl2(1-249) (Ho, 2004).

As used herein, a "single-strand ligase" is a DNA or RNA ligase enzyme that is active on single-stranded DNA or RNA molecules.

As used herein, the terms "buffer" or "buffering agents" refer to materials that, when added to a solution, cause the solution to resist changes in pH. As used herein, the term "reaction buffer" refers to a buffering solution in which an enzymatic or chemical reaction is performed.

The terms "isolated" or "purified" when used in relation to a polynucleotide or nucleic acid, as in "isolated RNA" or "purified RNA" refers to a nucleic acid that is identified and separated from at least one contaminant with which it is ordinarily associated in its source. Thus, an isolated or purified nucleic acid (e.g., DNA and RNA) is present in a form or setting different from that in which it is found in nature, or a form or setting different from that which existed prior to subjecting it to a treatment or purification method. For example, a given DNA sequence (e.g., a gene) is found on the host cell chromosome together with other genes as well as structural and functional proteins, and a specific RNA (e.g., a specific mRNA encoding a specific protein), is found in the cell as a mixture with numerous other RNAs and other cellular components. The isolated or purified polynucleotide or nucleic acid may be present in single-stranded or double-stranded form.

EXAMPLES

The following examples serve to illustrate certain preferred embodiments and aspects of the present invention and are not to be construed as limiting the scope thereof. Those skilled in the art will appreciate that many changes could be made in the specific embodiments disclosed herein while still obtaining an identical or similar result, without departing from the scope of the present invention.

Example 1

A Single-Tube Reaction to Sequentially Block the 3' End and Activate the 5' End of a Single-Stranded Oligodeoxyribonucleotide In this example, a synthetic DNA oligonucleotide (SEQ ID NO. 1) was purchased from Integrated DNA Technologies (Coralville, Iowa), with hydroxyl groups at both the 5' and 3' ends. This is a "standard" synthetic oligonucleotide, i.e., no chemical modifications were requested to be made to the 5' and 3' ends, or to the internal nucleotides.

SEQ ID NO. 1:   5'-GAGCGGCCGCGAAGATCAGA-3'

The overall reaction involved three steps that were performed sequentially in the same reaction vessel.

Step 1: The first step was performed to block the 3' end of the DNA oligonucleotide by reaction with TdT in the presence of ddATP. The following components were added in a 0.2-mL sterile microcentrifuge tube:

| Component | Volume | Final Concentration |
|---|---|---|
| Nuclease-Free Water | 8 µL | — |
| 10X CircLigase Buffer | 4 µL | 1X |
| ddATP (1 mM) | 4 µL | 100 µM |
| DNA oligonucleotide SEQ ID NO. 1 (10 µM) | 20 µL | 5 µM |
| TdT (3,200 U/mL) | 4 µL | 0.32 U/µL |
| Total Volume | 40 µL | — |

The reaction was incubated at 37° C. for 15 minutes. A 1-4 aliquot was removed for analysis, to which was added 4 µL of Nuclease-Free Water and 5 µL of Loading Dye. This was labeled Sample 1.

Step 2: To the remaining reaction mixture (39 µL), the following components were added:

| Component | Volume | Final Concentration |
|---|---|---|
| Nuclease-Free Water | 44 µL | — |
| 10X CircLigase Buffer | 6 µL | 1X |
| T4 Polynucleotide Kinase (10 U/µL) | 1 µL | 0.1 U/µL |
| ATP (10 mM) | 10 µL | 1 mM |
| Total Volume | 100 µL | — |

The reaction was incubated at 37° C. for 15 minutes. A 2.5-4 aliquot was removed for analysis, to which was added 2.5 µL of Nuclease-Free Water and 5 µL of Loading Dye. This was labeled Sample 2.

Step 3: To the remaining reaction mixture (97.5 µL), the following components were added:

| Component | Volume | Final Concentration |
|---|---|---|
| Nuclease-Free Water | 62.5 µL | — |
| 10X CircLigase Buffer | 10 µL | 1X |

-continued

| Component | Volume | Final Concentration |
|---|---|---|
| CircLigase ssDNA Ligase (22 μM) | 20 μL | 2.2 μM |
| ATP (10 mM) | 10 μL | 1 mM |

The reaction was incubated at 60° C. for 2 hours. A 5-μL aliquot was removed for analysis, to which was added 5 μL of Loading Dye. This was labeled Sample 3.

Figure 3:
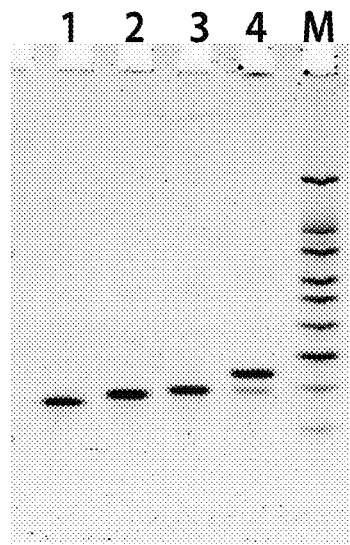
FIG. 3 is a picture of a gel illustrating the results of a method employing a single-tube enzymatic reaction to sequentially block the 3' end and activate the 5' end of a ssDNA oligonucleotide.

The samples were analyzed by electrophoresis on a 16% polyacrylamide/8 M urea gel in 1× Tris-borate-EDTA (TBE) buffer. The results are shown in FIG. 3. The observed shift in mobility of the DNA oligonucleotide is consistent with the expected change in the 3'- and 5'-terminal groups at each stage. The example demonstrates that a ss DNA oligonucleotide (lane 1) can be 3'-blocked (lane 2), 5'-phosphorylated (lane 3), and 5'-adenylated (lane 4) in a rapid and efficient manner in a single-tube reaction using the methods disclosed herein.

Example 2

A Single-Tube Reaction to Activate the 5' End of a Single-Stranded DNA Oligonucleotide that is Chemically Blocked at the 3' End Example 1 showed that a single-stranded DNA oligonucleotide can be 3'-end-blocked and 5'-end-activated enzymatically following the protocol disclosed. However, if the 3' end of the DNA oligonucleotide is chemically blocked during oligonucleotide synthesis, the 5' end can be activated by performing steps 2 and 3 in a single-tube reaction. This example illustrates the activation of the 5' end of a synthetic, ss DNA oligonucleotide (SEQ ID NO. 2) containing a 3'-amino modifier (3'Am) as a blocking group. In this example, the 5' end is phosphorylated and adenylated in a single-tube reaction that contains all the required components and enzymes.

SEQ ID NO. 2:    5'-TCGTATGCCGTCTTCTGCTTG/3Am/-3'

The following components were added in a 0.2-mL sterile microcentrifuge tube:

| Component | Volume | Final Concentration |
|---|---|---|
| Nuclease-Free Water | 26.5 μL | — |
| 10X CircLigase Buffer | 5 μL | 1X |
| DNA oligonucleotide SEQ ID NO. 2 (10 μM) | 5 μL | 1 μM |
| T4 Polynucleotide Kinase (10 U/μL) | 1 μL | 0.1 U/μL |
| ATP (10 mM) | 5 μL | 1 mM |
| MnCl₂ (50 mM) | 2.5 μL | 2.5 mM |
| CircLigase ssDNA Ligase (22 μM) | 5 μL | 2.2 μM |
| Total Volume | 50 μL | — |

Figure 4:
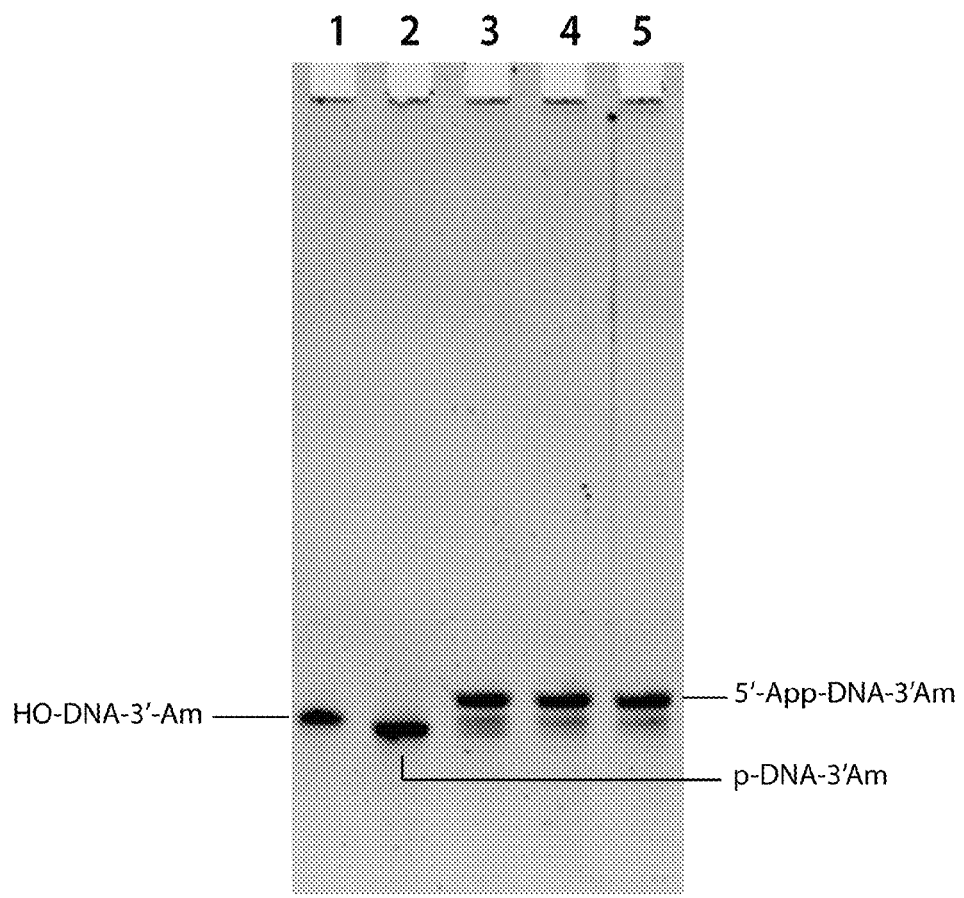
FIG. 4 is a picture of a gel illustrating enzymatic activation of the 5' end of a 3'-blocked ssDNA oligonucleotide.

The reaction mixture was incubated at 37° C. for 15 minutes and then at 60° C.; aliquots of the reaction mixture were withdrawn at time points of 2, 4, and 16 hours and mixed with DNA loading dye for further analysis. The samples were analyzed by electrophoresis on a 16% polyacrylamide/8 M urea gel in 1×TBE buffer. The results are shown in FIG. 4. As observed by the change in mobility, the reaction results in a majority of the 3'-blocked DNA oligonucleotide being adenylated after a 4-hour incubation, and the reaction is not made appreciably more efficient by extending the incubation time to 16 hours.

Example 3

Enzymatic Degradation of 5'-Adenylated, 3'-Blocked DNA Oligonucleotide

In this example, sequential enzymatic treatment with TAP and RecJ Exonuclease is used to degrade a 5'-adenylated, 3'-blocked DNA oligonucleotide (5'-App-DNA-X). Control reactions are also performed using a 5'-phosphorylated, 3'-blocked DNA oligonucleotide (5'-p-DNA-X). These modified oligonucleotides were prepared as described below from a DNA oligonucleotide purchased from TriLink Biotechnologies (San Diego, Calif.) with a 3'-terminal nucleotide that has a 2'-O-methyl group and a C3 spacer moiety (SEQ ID NO. 3).

SEQ ID NO. 3:    5'-GACGAAGACAGTAGACANNNNNNN-(2'O-Me)
                 (N-propyl)-3'

5'-p-DNA-X was prepared following a procedure similar to that described in Example 1, Step 2, starting with 250 pmol of SEQ ID NO. 3. 5'-App-DNA-X was prepared following a procedure similar to that described in Example 1, Steps 2 and 3, starting with 250 pmol of SEQ ID NO. 3. After the reactions, the nucleic acid was purified by phenol and chloroform extractions, followed by gel-filtration spin-column chromatography.

The following reactions were set up using 5 pmol (1 μL) of 5'-p-DNA-X and 5'-App-DNA-X.

1. 5'-p-DNA-X (control)
2. 5'-App-DNA-X (control)
3. 5'-p-DNA-X+RecJ
4. 5'-App-DNA-X+RecJ
5. 5'-p-DNA-X+TAP
6. 5'-App-DNA-X+TAP
7. 5'-p-DNA-X+TAP+RecJ
8. 5'-App-DNA-X+TAP+RecJ For reactions 1-4, the following components were added in sterile 0.2-mL microcentrifuge tubes:

| Component | Volume per Reaction |
|---|---|
| Nuclease-Free Water | 2.5 μL |
| 20X T4RL2 Buffer | 0.25 μL |
| Tris•Cl (pH 9.0) (0.5M) | 0.25 μL |
| DTT (100 mM) | 0.5 μL |
| 5'-p-DNA-X or 5'-App-DNA-X (5 μM) | 1.0 μL |
| Total Volume | 4.5 μL |

The composition of 20× T4RL2 Buffer was 1 M Tris-acetate, pH 6.0, 50 mM magnesium chloride. To reactions 1 and 2, 0.5 μL of Nuclease-Free Water was added (control reactions). To reactions 3 and 4, 5 U of RecJ Exonuclease was added. The reactions were incubated at 37° C. for 1 hour.

For reactions 5-6, the following components were added in sterile 0.2-mL microcentrifuge tubes:

| Component | Volume per Reaction |
|---|---|
| Nuclease-Free Water | 0.75 μL |
| 20X T4RL2 Buffer | 0.25 μL |
| EDTA (50 mM) | 1.0 μL |
| DTT (100 mM) | 0.5 μL |
| TAP (10 U/uL) | 0.5 μL |
| Total Volume | 3.0 μL |

The pH of the above reaction mixture was approximately 6.0. To reaction 5, 2 μL (10 pmol) of 5'-p-DNA-X was added; to reaction 6, 2 μL (10 pmol) of 5'-App-DNA-X was added. The reactions were incubated at 37° C. for 1 hour.

From each of reactions 5 and 6, 2.5-μL aliquots were transferred to fresh 0.2-mL microcentrifuge tubes to prepare reactions 7 and 8, respectively. The following components were added.

| Component | Volume per Reaction |
|---|---|
| Nuclease-Free Water | 0.5 μL |
| Tris•Cl (pH 9.0) (0.5M) | 0.5 μL |
| MgCl$_2$ (100 mM) | 1.0 μL |
| RecJ Exonuclease (10 U/μL) | 0.5 μL |
| Total Volume | 2.5 μL |

The reactions were incubated at 37° C. for 1 hour. To the remaining 2.5 μL of reactions 5 and 6 was added 2.5 μL of Nuclease-Free Water. All the reactions 1-8 were terminated by the addition of 5 μL of formamide loading dye and incubation at 90° C. for 30 seconds. For each of reactions 1-8, a 2-μL aliquot was analyzed by electrophoresis on a 16% polyacrylamide/8 M urea gel in 1× TBE buffer.

Figure 5:
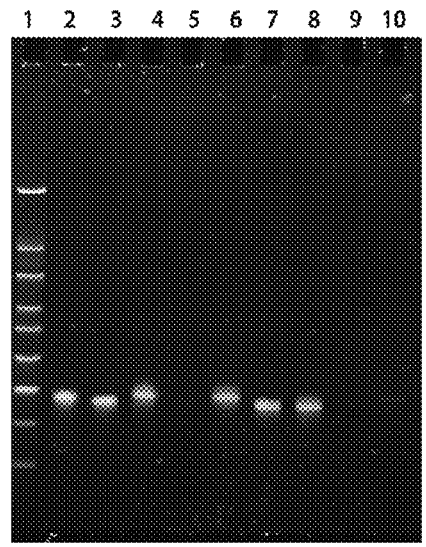
FIG. 5 is a picture of a gel illustrating enzymatic degradation of a 5'-adenylated, 3'-blocked DNA oligonucleotide by sequential treatment with TAP and RecJ Exonuclease.

The results are shown in FIG. 5. By comparing lanes 5 and 6, it is evident that 5'-App-DNA-X is resistant to the 5' to 3' exonuclease activity of RecJ Exonuclease, but 5'-p-DNA-X is not. From lanes 7-10, it is apparent that: i) 5'-App-DNA-X is converted to 5'-p-DNA-X by TAP, and ii) 5'-p-DNA-X can be subsequently degraded by RecJ Exonuclease. Thus, the example demonstrates that a single-tube reaction comprising sequential treatment with TAP and RecJ Exonuclease can be used to remove 5'-App-DNA-X from a reaction mixture.

Example 4

3'-End Tagging of RNA and Removal of Excess Tagging Oligonucleotide in a Single-Tube Reaction without Intervening Gel Purification For this example, a synthetic small-RNA molecule (SEQ ID NO. 4) was used to demonstrate the 3'-end-tagging process. The tagging DNA oligonucleotide (SEQ ID NO. 2) was adenylated as in Example 2 (5'-App-DNA-X). The RNA ligase enzyme used was truncated T4 RNA Ligase 2, or Rnl2 (1-249).

SEQ ID NO. 4: 5'-pUrUrCrGrCrUrUrGrCrArGrArGrArGr
ArArArUrCrArC-3'

The following reactions were set up:
1. small RNA
2. small RNA+Rnl2(1-249)
3. 5'-App-DNA-X
4. 5'-App-DNA-X+Rnl2(1-249)
5. small RNA+5'-App-DNA-X+Rnl2(1-249)
6. [small RNA+5'-App-DNA-X+APex™ Alkaline Phosphatase]+Rnl2(1-249)

A mastermix of reaction components was prepared as follows:

| Component | For 1 Reaction | For 8 Reactions | Final Concentration |
|---|---|---|---|
| Nuclease-Free Water | 2.75 μL | 22 μL | — |
| 20X T4RL2 Buffer | 0.5 μL | 4 μL | 1X |
| DTT (100 mM) | 0.5 μL | 4 μL | 5 mM |
| RiboGuard™ RNase Inhibitor | 0.25 μL | 2 μL | 10 U |
| PEG-8000 (50%) | 2.0 μL | 16 μL | 10% |
| Total Volume | 6.0 μL | 48 μL | — |

A 12-μL aliquot of the mastermix was added to Reaction 1, followed by 2 μL of the small RNA and 4 μL of Nuclease-Free Water. The reaction was mixed and 9.0 μL was transferred to Reaction 2.

A 12-μL aliquot of the mastermix was added to Reaction 3, followed by 2 μL of 5'-App-DNA-X and 4 μL of Nuclease-Free Water. The reaction was mixed and 9.0 μL was transferred to Reaction 4.

A 12-μL aliquot of the mastermix was added to Reaction 5, followed by 2 μL each of small RNA and 5'-App-DNA-X. The reaction was mixed and 8.0 μL was transferred to Reaction 6.

To Reaction 5, 0.5 μL of Nuclease-Free water was added. To Reaction 6, 0.5 μL of Apex Alkaline Phosphatase was added. Both reactions were incubated at room temperature (~22° C.) for 10 minutes.

To Reactions 1, 3, and 5, 1 μL of Nuclease-Free water was added. To Reactions 2, 4, and 6, 1 μL of Rnl2(1-249) was added. All reactions were incubated at room temperature for 3 hours, after which 2.5-μL aliquots were removed from each reaction and transferred to labeled tubes. To these tubes was added 2.5 μL of formamide loading dye and the samples were frozen.

To each of the remaining 7.5 μL of Reactions 1-6, the following components were added:

| Component | Volume |
|---|---|
| Nuclease-Free Water | 0.5 μL |
| EDTA (50 mM) | 1.0 μL |
| TAP (10 U/μL) | 1.0 μL |
| Total Volume | 2.5 μL |

The reactions were incubated at 37° C. for 1 hour, after which the following components were added:

| Component | Volume |
|---|---|
| Tris•Cl (pH 9.0) (500 mM) | 1.0 μL |
| MgCl$_2$ (50 mM) | 3.0 μL |
| RecJ Exonuclease (10 U/μL) | 1.0 μL |
| Total Volume | 5.0 μL |

Figure 6:
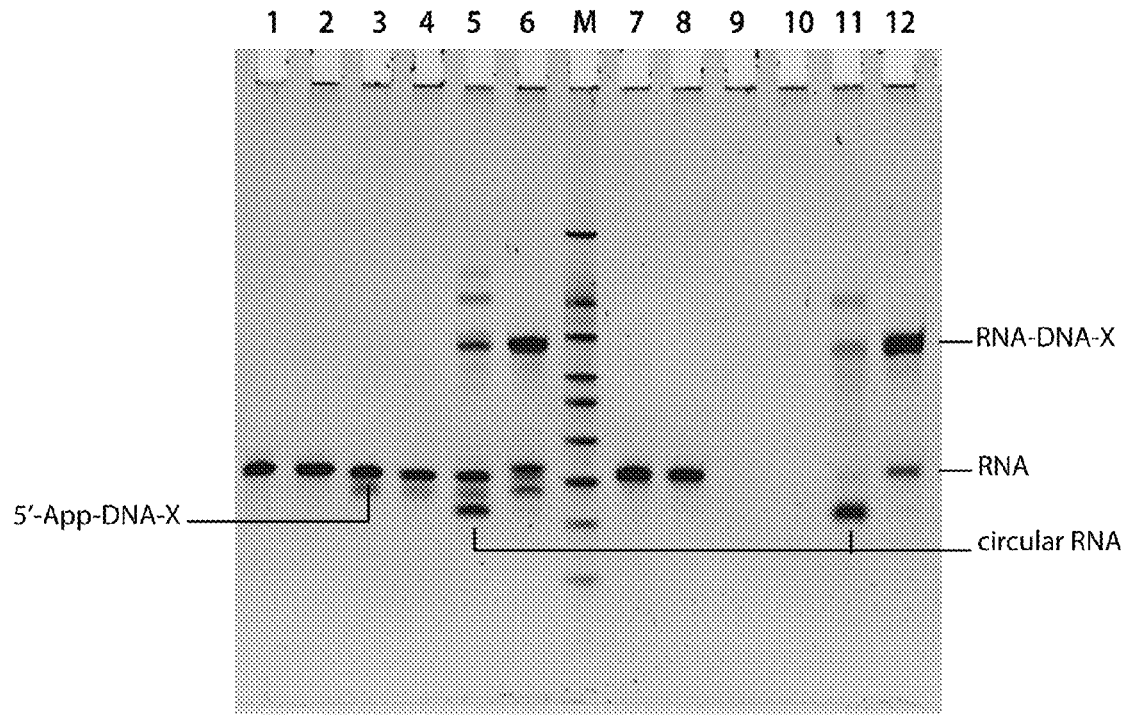
FIG. 6 is a picture of a gel illustrating 3'-end-tagging of RNA and removal of excess tagging oligonucleotide in a single-tube reaction without intervening gel purification.

The reactions were incubated at 37° C. for 1 hour, after which 5.0 μL aliquots were removed and 2.5 μL of formamide loading dye was added. All samples were heated at 70° C. for 30 seconds. Samples were analyzed by electrophoresis on a 16% polyacrylamide/8 M urea gel in 1× TBE buffer. The results are shown in FIG. 6.

The example demonstrates that 3'-end-tagging of RNA and removal of excess tagging molecules can be performed in single-tube format, without any intervening clean-up steps.

Example 5

Figure 8:
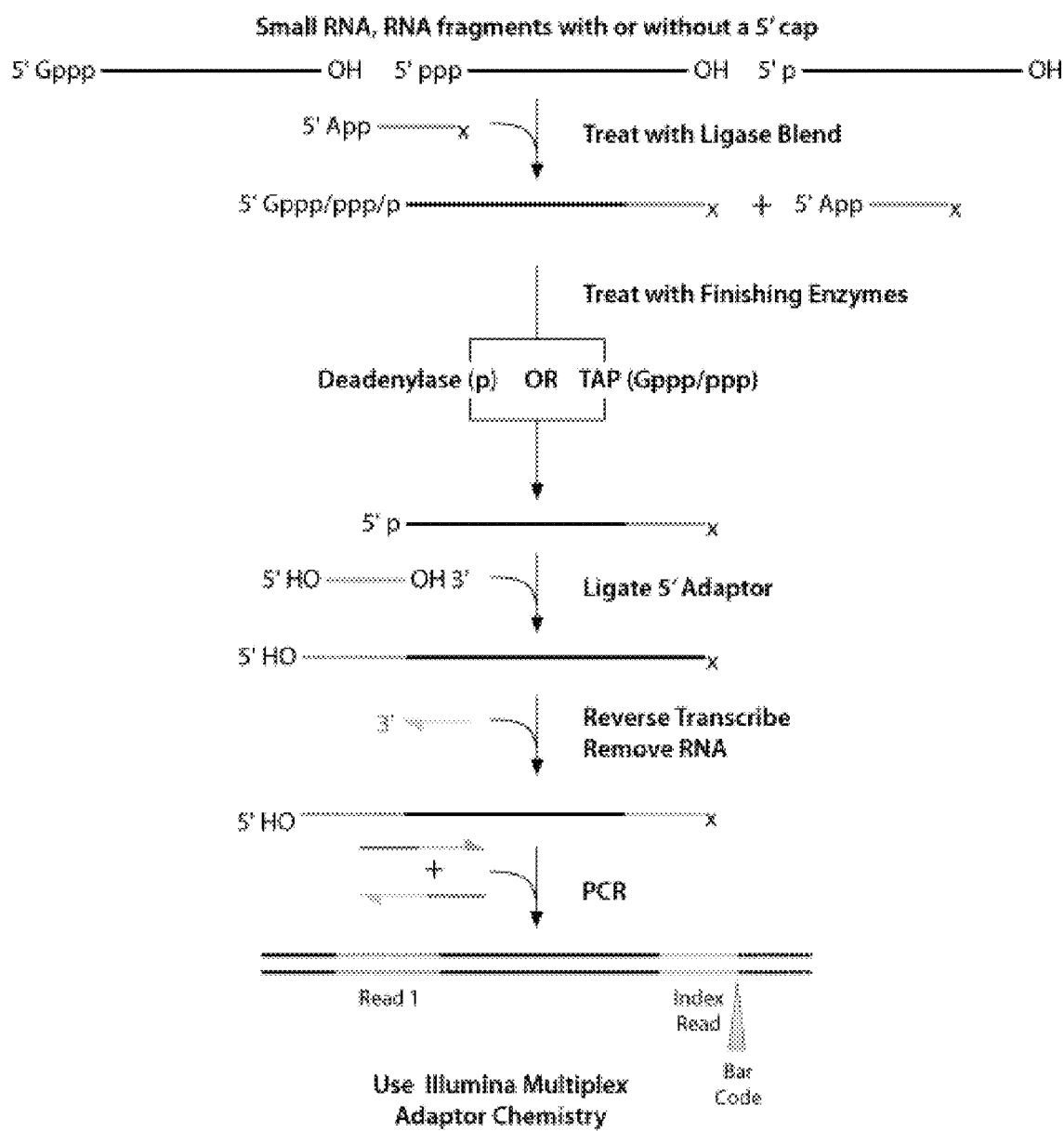
FIG. 8 is an illustration of an exemplary embodiment of the described methods for preparing an end-tagged ds cDNA library from RNA, and preparing the resulting sequences for use in ILLUMINA's multiplex adapter chemistry.

This Examples describes the preparation of a ds cDNA library from small-RNA and total RNA samples for sequencing on Illumina Genome Analyzer, using the steps outlined in FIG. 1, FIG. 8, and the methods described in Example 4.

For this example, a synthetic small-RNA molecule (RNA control oligo: SEQ ID NO. 5), Universal Human Reference total RNA (UHRR; Stratagene, La Jolla, Calif.), and Human Brain Reference total RNA (BrRR; Ambion, Austin, Tex.) were used to prepare a cDNA library tagged at the 5' and 3' ends.

```
SEQ ID NO. 5:   5'-p-NrNrCrGrCrUrUrGrCrArGrArGrAr
                GrArArArUrCrNrN-OH-3'
```

For library preparation in this example, the following synthetic oligonucleotides were used: 3'-end-tagging DNA adaptor (SEQ ID NO. 6), 5'-end-tagging RNA adaptor (SEQ ID NO. 7), reverse transcription and PCR reverse primer (SEQ ID NO. 8), and PCR forward primer (SEQ ID NO. 9).

```
SEQ ID NO. 6:   5'-App/TCGTATGCCGTCTTCTGCTTG/3'ddC

SEQ ID NO. 7:   5'-HO-GrUrUrCrArGrArGrUrUrCrUrArCr
                ArGrUrCrCrGrArCrGrArUrC-OH-3'

SEQ ID NO. 8:   5'-CAAGCAGAAGACGGCATACGA-3'

SEQ ID NO. 9:   5'-AATGATACGGCGACCACCGACAGGTTCAGAG
                TTCTACAGTCCGACG-3'
```

The following reactions were set up:
1. Control: No RNA
2. RNA control oligo (1 pmol)
3. RNA control oligo (0.1 pmol)
4. RNA control oligo (0.01 pmol)
5. UHRR (1 μg)
6. UHRR (5 μg)
7. BrRR (1 μg)
8. BrRR (5 μg)

Step 1: 3'-Adaptor Ligation

For sample 1, 8 μL of nuclease-free water was added. For samples 2-7, nuclease-free water was added to a final volume of 8 μL. A 3'-adaptor ligation mastermix was prepared as follows:

| Component | For 1 Reaction | For 10 Reactions | Final Concentration |
|---|---|---|---|
| 20X T4RL2 buffer | 0.75 μL | 7.5 μL | 1X (2.5 mM Mg$^{2+}$) |
| DTT (100 mM) | 0.75 μL | 7.5 μL | 5 mM |
| RiboGuard ™ RNase Inhibitor | 0.5 μL | 5.0 μL | 10 U |
| PEG-8000 (50%) | 3.0 μL | 30.0 μL | 10% |
| 3'-end-tagging DNA adaptor (20.0 μM) | 1.0 μL | 10.0 μL | 20 pmol |
| Total | 6.0 μL | 60.0 μL | — |

A 6-μL aliquot of the mastermix was added to each of Reactions 1-8, and the samples were gently mixed by vortexing. Next, 1 μL of an enzyme mixture containing truncated T4 RNA Ligase 2 and T4 RNA Ligase was added to each reaction. The reactions were incubated for 2 hours at 25° C.

Step 2: Removal of Excess 3' Adaptor

To each reaction from Step 1, 4.0 μL of EDTA (25 mM) was added. The reactions were mixed thoroughly and centrifuged. TAP (1 μL; 10 U) was added to each reaction, and the samples were mixed by pipetting. The samples were incubated for 1 hour at 37° C.

A mastermix of reaction components was prepared as follows:

| Component | Volume | Final Concentration |
|---|---|---|
| Tris•Cl (pH 9.0) (500 mM) | 2.0 μL | 40 mM |
| MgCl$_2$ (50 mM) | 7.0 μL | ~11.7 mM |
| RecJ Exonuclease (10 U/μL) | 1.0 μL | 10 U |
| Total | 10.0 μL | — |

A 10-μL aliquot of the mastermix was added to each reaction, and the samples were incubated for 30 minutes at 37° C.

Step 3: Ligation of 5' Adaptor

A mastermix of reaction components was prepared as follows:

| Component | Volume | Final Concentration |
|---|---|---|
| RNA Ligase Buffer | 1.0 μL | |
| PEG 8000 (50%) | 5.0 μL | ~11.7 mM |
| ATP (10 mM) | 1.0 μL | 250 mM |
| 5' RNA adaptor (10 mM) | 2.0 μL | 20 pmol/rxn |
| T4 RNA Ligase (5 U/μL) | 1.0 μL | 5 U |
| Total | 10.0 μL | — |

A 10-μL aliquot of the mastermix was added to each reaction from Step 2, and the samples were incubated for an hour at 25° C. To each sample, 10 μL of nuclease-free water was added, bringing the total volume of each sample to 50 pt.

Step 4: Purification of Ligation Products

The samples from Step 3 were purified using a RNA Clean & Contentrator™ Kit (Zymo Research, Orange, Calif.; Cat No. R1015, 1016) according to the manufacturer's instructions for total RNA (>17 nucleotides). The ligation products were eluted with 30 μL of nuclease-free water for each reaction.

Step 5: Reverse Transcription

A mastermix of reaction components was prepared as follows:

| Component | Volume | Final Concentration |
|---|---|---|
| MMLV Buffer (10X) | 4.0 μl | 1X |
| dNTPs (10 mM each) | 2.0 μl | 0.5 mM |
| DTT (100 mM) | 2.0 μl | 5 mM |
| RT Primer (20 mM) | 1.0 μl | 0.5 mM |
| MMLV RT HP (200 U/μl) | 1.0 μl | 200 U |
| Total | 10.0 μl | — |

A 10-μL aliquot of the mastermix was added to each of the reactions from Step 4. The samples were incubated for 15 minutes at 37° C., followed by 15 minutes at 85° C. A 1-μL aliquot of RNase Mix was added to each reaction, and the samples were incubated for 5 minutes at 55° C.

Step 6: PCR Amplification

A 5-μL aliquot was removed from each reaction from Step 5 (cDNA), and the following components were added:

| Component | Volume |
|---|---|
| (5 μL cDNA + nuclease-free water) | 45 μL |
| 2X FailSafe ™ Buffer E | 50 μL |
| PCR forward primer (20 μM) | 2.0 μL |
| PCR reverse primer (20 μM) | 2.0 μL |
| FailSafe ™ Enzyme Mix | 1.0 μL |
| Total | 100 μL |

The samples were incubated for 30 seconds at 95° C., then 12 cycles of PCR were performed (15 seconds at 94° C.; 5 seconds at 55° C.; 5 seconds at 65° C.). A 5-4 aliquot was removed from each sample, mixed with DNA loading dye, and analyzed by electrophoresis in a 8% nondenaturing polyacrylamide gel in 1× TBE buffer.

Figure 7:
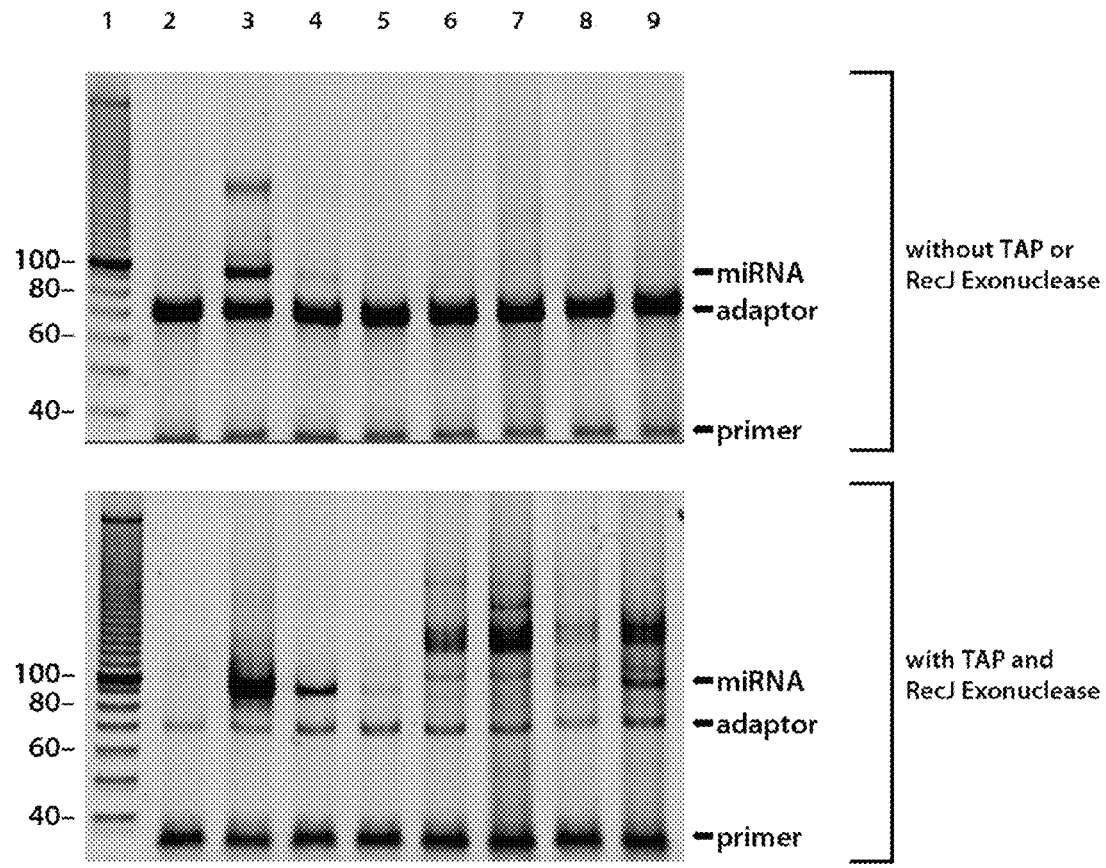
FIG. 7 is a picture of a gel illustrating the decrease in amount of undesired adaptor-dimer ligation product, following enzymatic removal of the excess adaptor with TAP and RecJ Exonuclease as outlined in FIG. 1, thereby improving the sensitivity of detection of adaptor-tagged small-RNA products.

A similar set of libraries was prepared by the procedure described in this example, but omitting Step 2. The samples were analyzed by electrophoresis in a 8% nondenaturing polyacrylamide gel in 1× TBE buffer. The results are shown in FIG. 7.

The libraries prepared in this example from UHRR and BrRR, were sequenced on an Illumina GAIIx platform and the data processed using the CLC Genomics Workbench software to map tags of known miRNA sequences. For the UHRR sample, a total of 7,823,532 individual reads mapped to the human genome (hg19) and 1,612,429 reads matched known miRNAs based upon the Sanger miRBase version 15 annotation. The BrRR sample produced 16,823,979 total reads mapping to hg19 and 7,582,626 reads that matched known miRNAs. Raw tags counts were normalized using a "tags per million reads" approach (tpm=reads matching miR×1,000,000/total reads matching genome) and sorted from largest to smallest values. Only the top one hundred highest detected/expressed miRNAs are shown for both the UHRR and BrRR samples in Table 1.

TABLE 1

Top 100 Highest Expressed miRNAs in UHRR

| miRNA | UHRR (tpm) |
|---|---|
| hsa_miR_92 | 33611.3 |
| hsa_miR_181a | 17225.5 |
| hsa_let_7a | 14054.9 |
| hsa_miR_125b | 8568.8 |

TABLE 1-continued

| hsa_let_7i | 7994.9 |
|---|---|
| hsa_miR_24 | 7313.2 |
| hsa_miR_146a | 6076.2 |
| hsa_miR_21 | 5607.8 |
| hsa_miR_92b | 4949.9 |
| hsa_miR_191 | 4738.3 |
| hsa_miR_15b | 4459.9 |
| hsa_let_7b | 4448.5 |
| hsa_miR_200c | 3315.8 |
| hsa_miR_423 | 2907.3 |
| hsa_miR_302a_AS | 2889.1 |
| hsa_let_7g | 2687.0 |
| mmu_miR_93 | 2636.4 |
| hsa_miR_25 | 2421.2 |
| hsa_miR_302d | 2375.4 |
| hsa_miR_331 | 2366.6 |
| hsa_miR_100 | 2300.8 |
| hsa_miR_30c | 2195.9 |
| rno_miR_422b | 2180.6 |
| hsa_miR_23a | 2156.8 |
| hsa_miR_302a | 1838.4 |
| hsa_miR_302b | 1769.7 |
| mmu_let_7a | 1718.3 |
| hsa_miR_186 | 1679.9 |
| hsa_miR_425_5p | 1634.0 |
| hsa_miR_146b | 1516.5 |
| hsa_miR_182 | 1398.6 |
| hsa_miR_99b | 1397.5 |
| mmu_miR_151 | 1377.3 |
| hsa_miR_27b | 1300.3 |
| hsa_miR_26a | 1298.1 |
| hsa_miR_222 | 1291.0 |
| hsa_miR_103 | 1177.6 |
| hsa_miR_148b | 1158.8 |
| hsa_miR_16 | 1130.1 |
| mmu_miR_221 | 1093.6 |
| hsa_let_7d | 1089.7 |
| mmu_miR_106a | 1055.8 |
| hsa_miR_210 | 1047.5 |
| hsa_miR_197 | 1046.7 |
| hsa_let_7f | 1045.4 |
| hsa_miR_125a | 1022.2 |
| hsa_let_7c | 866.9 |
| hsa_miR_342 | 836.3 |
| hsa_miR_29a | 813.1 |
| hsa_miR_484 | 793.9 |
| hsa_miR_320 | 778.7 |
| hsa_miR_26b | 724.9 |
| hsa_miR_193b | 700.1 |
| hsa_miR_221 | 698.5 |
| mmu_miR_744 | 669.9 |
| hsa_miR_20a | 647.9 |
| rno_miR_151_AS | 612.8 |
| hsa_miR_106b | 606.8 |
| hsa_miR_30b | 604.7 |
| hsa_miR_339 | 602.4 |
| hsa_miR_148a | 581.6 |
| hsa_miR_365 | 559.0 |
| hsa_miR_181b | 539.0 |
| hsa_miR_126 | 520.2 |
| hsa_miR_27a | 508.8 |
| hsa_miR_211 | 474.7 |
| hsa_miR_30d | 454.7 |
| hsa_miR_194 | 406.0 |
| hsa_miR_183 | 402.9 |
| hsa_miR_200b | 399.9 |
| hsa_miR_23b | 391.6 |
| hsa_miR_34a | 381.9 |
| hsa_miR_152 | 380.4 |
| hsa_miR_361 | 379.5 |
| hsa_miR_574 | 361.9 |
| mmu_let_7d_AS | 353.9 |
| hsa_miR_486 | 339.9 |
| hsa_miR_10b | 316.4 |
| hsa_miR_99a | 310.3 |
| hsa_miR_22 | 309.7 |
| hsa_miR_130b | 273.2 |
| hsa_miR_18a_AS | 270.1 |
| mmu_miR_124a | 261.4 |
| hsa_miR_205 | 258.5 |

TABLE 1-continued

| miRNA | Value |
|---|---|
| hsa_miR_149 | 245.3 |
| hsa_miR_17_5p | 237.1 |
| mmu_miR_326 | 217.0 |
| hsa_miR_324_5p | 196.1 |
| mmu_miR_302d | 193.9 |
| hsa_miR_185 | 193.4 |
| mmu_miR_720 | 192.1 |
| mmu_miR_374_5p | 171.3 |
| hsa_miR_128a | 166.3 |
| mmu_let_7f | 164.2 |
| hsa_miR_19b | 148.1 |
| hsa_miR_296 | 141.0 |
| hsa_miR_15a | 139.2 |
| hsa_miR_483 | 138.3 |
| hsa_miR_184 | 135.9 |
| hsa_miR_328 | 121.2 |

Top 100 Highest Expressed miRNAs in BrRR

| miRNA | BrRR (tpm) |
|---|---|
| mmu_miR_124a | 47803.1 |
| hsa_let_7a | 42263.0 |
| hsa_miR_181a | 35719.0 |
| hsa_miR_125b | 18748.5 |
| hsa_miR_9 | 15257.4 |
| hsa_miR_26a | 15045.0 |
| hsa_let_7g | 13336.1 |
| mmu_let_7a | 12738.5 |
| hsa_let_7b | 11258.0 |
| hsa_miR_30c | 10679.5 |
| hsa_let_7f | 9340.6 |
| hsa_miR_143 | 8487.5 |
| hsa_let_7i | 8303.3 |
| hsa_miR_27b | 7866.5 |
| hsa_miR_24 | 7584.1 |
| hsa_miR_124a | 6633.1 |
| mmu_miR_9 | 6390.5 |
| hsa_miR_218 | 6268.1 |
| hsa_miR_29a | 5995.8 |
| hsa_miR_126 | 5833.8 |
| hsa_miR_128a | 5498.9 |
| hsa_let_7c | 4752.6 |
| mmu_let_7f | 4428.5 |
| hsa_miR_99a | 4121.0 |
| hsa_miR_191 | 4056.7 |
| hsa_miR_30b | 3937.6 |
| hsa_let_7d | 3801.4 |
| hsa_miR_16 | 3482.8 |
| hsa_miR_148b | 3348.6 |
| hsa_miR_331 | 3314.6 |
| hsa_miR_598 | 3191.8 |
| hsa_miR_23b | 3173.6 |
| hsa_miR_139 | 2999.9 |
| hsa_miR_99b | 2799.3 |
| hsa_miR_103 | 2736.2 |
| hsa_miR_26b | 2567.5 |
| hsa_miR_125a | 2540.0 |
| hsa_miR_204 | 2418.6 |
| hsa_miR_29c | 2346.1 |
| mmu_miR_451 | 2238.1 |
| hsa_miR_149 | 2183.1 |
| hsa_miR_21 | 2135.8 |
| hsa_miR_181b | 2134.9 |
| hsa_miR_379 | 2129.3 |
| hsa_miR_92b | 2121.4 |
| mmu_miR_129_3p | 1949.8 |
| hsa_miR_30e_5p | 1919.6 |
| hsa_miR_100 | 1784.1 |
| mmu_miR_151 | 1779.9 |
| hsa_miR_425_5p | 1628.4 |
| hsa_miR_92 | 1537.4 |
| hsa_miR_195 | 1520.7 |
| hsa_miR_29b | 1509.6 |
| hsa_miR_423 | 1483.9 |
| hsa_miR_127 | 1471.4 |
| hsa_miR_9_AS | 1405.5 |
| hsa_miR_153 | 1402.9 |
| hsa_miR_138 | 1400.0 |
| hsa_miR_98 | 1397.8 |
| rno_miR_151_AS | 1378.9 |
| hsa_miR_197 | 1331.8 |
| hsa_miR_328 | 1316.2 |
| hsa_miR_135a | 1303.1 |
| hsa_miR_342 | 1233.3 |
| hsa_miR_30d | 1211.2 |
| hsa_miR_23a | 1164.4 |
| hsa_miR_186 | 1163.9 |
| mmu_let_7d_AS | 1124.3 |
| mmu_miR_374_5p | 1086.4 |
| hsa_miR_485_3p | 1081.6 |
| hsa_miR_15a | 1011.8 |
| hsa_miR_146b | 1009.4 |
| mmu_miR_153 | 955.4 |
| mmu_miR_744 | 935.8 |
| rno_miR_422b | 909.0 |
| mmu_miR_495 | 881.0 |
| mmu_miR_221 | 834.8 |
| mmu_miR_326 | 811.5 |
| hsa_miR_128b | 798.9 |
| hsa_miR_181c | 755.6 |
| hsa_miR_374 | 742.9 |
| hsa_miR_487b | 701.5 |
| hsa_miR_451 | 699.0 |
| hsa_let_7e | 655.3 |
| hsa_miR_330 | 643.2 |
| mmu_miR_376c | 642.1 |
| hsa_miR_22 | 640.9 |
| hsa_miR_135b | 617.5 |
| hsa_miR_484 | 617.5 |
| hsa_miR_185 | 585.2 |
| mmu_miR_379 | 562.4 |
| hsa_miR_221 | 554.7 |
| hsa_miR_361 | 554.4 |
| hsa_miR_34a | 532.6 |
| hsa_miR_497 | 530.3 |
| hsa_miR_329 | 507.5 |
| hsa_miR_30a_5p | 505.2 |
| hsa_miR_132 | 490.2 |
| hsa_miR_222 | 490.2 |
| hsa_miR_106b | 474.3 |

The example demonstrates that enzymatic treatment with TAP and RecJ Exonuclease substantially reduces the amount of excess adaptor-dimer products in the final cDNA libraries. Sequencing results from these libraries indicate that they provide valuable information for the detection and profiling of known miRNAs.

All publications and patents mentioned in the above specification and in the list of references below are herein incorporated by reference. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

Ahel, I et al. (2006) The neurodegenerative disease protein aprataxin resolves abortive DNA ligation intermediates. Nature 443:713-717.

Amara, R R and Vijaya, S. (1997) Specific polyadenylation and purification of total messenger RNA from *Escherichia coli*. Nucleic Acids Res. 25:3465-3470.

Carthew, R W and Sontheimer, E J. (2009) Origins and mechanisms of miRNAs and siRNAs. Cell 136: 642-655.

Cooper, D L and Marzluff, W F. (1977) Polyadenylation of RNA in a cell-free system from mouse myeloma cells. J. Biol. Chem. 253:8375-8380

Ebhardt, H A et al. (2005) Extensive 3' modification of plant small RNAs is modulated by helper component-proteinase expression. Proc. Natl. Acad. Sci. USA 102:13398-13403.

England, T E et al. (1977) Dinucleoside pyrophosphates are substrates for T4-induced RNA ligase. Proc. Natl. Acad. Sci. USA 74:4839-4842.

Feng, Y. and Cohen, S. (2000) Unpaired terminal nucleotides and 5' monophosphorylation govern 3' polyadenylation by Escherichia coli poly(A) polymerase I. Proc. Natl. Acad. Sci. USA 97:6415-6420.

Haber, M. (2008) The current status of cDNA cloning. Genomics 91:232-242.

Hafner, M et al. (2008) Identification of microRNAs and other small regulatory RNAs using cDNA library sequencing. Methods 44:3-12.

Han, E S et al. (2006) RecJ exonuclease: substrates, products and interaction with SSB. Nucleic Acids Res. 34:1084-1091.

Ho, C K and Shuman, S. (2002) Bacteriophage T4 RNA ligase 2 (gp24.1) exemplifies a family of RNA ligases found in all phylogenetic domains. Proc. Natl. Acad. Sci. USA 99:12709-12714.

Ho, C K et al. (2004) Structure and mechanism of RNA ligase. Structure 12:327-339.

Kawano, M et al. (2010) Reduction of non-insert sequence reads by dimer eliminator LNA oligonucleotide for small RNA deep sequencing. BioTechniques 49:751-755.

Lovett, S T and Kolodner, R D. (1989) Identification and purification of a single-stranded-DNA-specific exonuclease encoded by the recJ gene of Escherichia coli. Proc. Natl. Acad. Sci. USA 86:2627-2631.

Maruyama, K. and Sugano, S. (1994) Oligo-capping: a simple method to replace the cap structure of eukaryotic mRNAs with oligoribonucleotides. Gene 138: 171-174.

Nandakumar, J et al. (2004) RNA substrate specificity and structure-guided mutational analysis of bacteriophage T4 RNA ligase 2. J. Biol. Chem. 279:31337-31347.

Ponting, C P et al. (2009) Evolution and functions of long noncoding RNAs. Cell 136: 629-641.

Saito, K et al. (2007) Pimet, the Drosophila homolog of HENT, mediates 2'-O-methylation of Piwi-interacting RNAs at their 3' ends. Genes Dev. 21:1603-1608

Sambrook, J et al. (1989) Molecular cloning: a laboratory manual (2nd ed). Cold Spring Harbor Laboratory Press, Cold Spring Harbor, N.Y. pp 6.46.

Silverman, S. (2004) Practical and general synthesis of 5'-adenylated RNA (5'-AppRNA). RNA 10:731-746.

Steege, D. (2000) Emerging features of mRNA decay in bacteria. RNA 6:1079-1090.

Takada, S et al. (2006) Mouse microRNA profiles determined with a new and sensitive cloning method. Nucleic Acids Res. 34:e115.

Vigneault, F et al. (2008) Efficient microRNA capture and bar-coding via enzymatic oligonucleotide adenylation. Nature Meth. 5:777-779.

Yang, Z et al. (2005) HENT recognizes 21-24 nt small RNA duplexes and deposits a methyl group onto the 2' OH of the 3' terminal nucleotide. Nucleic Acids Res. 34:667-675.

Yu, B et al. (2005) Methylation as a crucial step in plant microRNA biogenesis. Science 307:932-936.

We claim:

1. A method for enzymatic removal of excess activated donor DNA oligonucleotide from a sample following a bimolecular ligation reaction catalyzed by a single strand ligase enzyme comprising:
   (A) incubating the sample with TAP under conditions such that the excess 5'-App-DNA oligonucleotide is converted to 5'-phosphorylated donor DNA oligonucleotide; and
   (B) incubating the sample from step (A) with a DNA nuclease enzyme under conditions such that the 5'-phosphorylated donor DNA oligonucleotide is converted to deoxynucleotide monophosphates,
   wherein the incubating the sample with said TAP and DNA nuclease enzyme occurs in the same reaction vessel.

2. The method of claim 1, wherein the bimolecular ligation reaction comprises an RNA acceptor that has a 3'-hydroxyl group and a DNA oligonucleotide donor that has a 5'-adenylated nucleotide but does not have a 3'-hydroxyl nucleotide (5'-App-DNA-X).

3. The method of claim 1, wherein excess is defined as a molar ratio of ligation donor to ligation acceptor that is greater than 1.0.

4. The method of claim 2, wherein the DNA oligonucleotide donor has a 3'-terminal dideoxynucleotide or a 3'-amino spacer.

5. The method of claim 1, wherein the single-strand ligase enzyme is T4 RNA Ligase 1, T4 RNA Ligase 2, truncated T4 RNA Ligase 2, a mixture comprising T4 RNA Ligase 1 and truncated T4 RNA Ligase 2, bacteriophage TS2126 ligase, or a ssDNA Ligase.

6. The method of claim 1, wherein the DNA nuclease enzyme is RecJ Exonuclease or Lambda Exonuclease.

7. The method of claim 6, wherein the RNA acceptor is a miRNA, a siRNA, a piRNA, or a synthetic RNA.

8. The method of claim 6, wherein the RNA acceptor is a prokaryotic RNA.

9. The method of claim 6, wherein the RNA acceptor is a degraded mRNA.

10. The method of claim 7, wherein the miRNA has a 2'-O-methyl group at its 3'-terminal nucleotide.

11. The method of claim 2, wherein the RNA acceptor is a plant miRNA.

12. The method of claim 4, wherein the DNA oligonucleotide donor contains a next-generation sequencing adaptor sequence.

13. The method of claim 4, wherein the DNA oligonucleotide donor contains a RNA polymerase promoter sequence.

14. The method of claim 4, wherein the DNA oligonucleotide donor contains a restriction endonuclease recognition sequence.

15. A method for enzymatic removal of excess activated donor DNA oligonucleotide from a sample following a bimolecular ligation reaction catalyzed by a single strand ligase enzyme comprising:
   (A) incubating the sample with TAP under conditions such that the excess 5-App-DNA oligonucleotide is converted to 5'-phosphorylated donor DNA oligonucleotide; and
   (B) incubating the sample from step (A) with a DNA nuclease enzyme under conditions such that the 5'-phosphorylated donor DNA oligonucleotide is converted to deoxynucleotide monophosphates,
   wherein steps (A) and (B) occur without intervening sample purification.

16. The method of claim 15, wherein the bimolecular ligation reaction comprises an RNA acceptor that has a 3'-hydroxyl group and a DNA oligonucleotide donor that has a 5'-adenylated nucleotide but does not have a 3'-hydroxyl nucleotide (5'-App-DNA-X).

17. The method of claim 15, wherein excess is defined as a molar ratio of ligation donor to ligation acceptor that is greater than 1.0.

18. The method of claim 16, wherein the DNA oligonucleotide donor has a 3'-terminal dideoxynucleotide or a 3'-amino spacer.

19. The method of claim 15, wherein the single-strand ligase enzyme is T4 RNA Ligase 1, T4 RNA Ligase 2, truncated T4 RNA Ligase 2, a mixture comprising T4 RNA Ligase 1 and truncated T4 RNA Ligase 2, bacteriophage TS2126 ligase, or a ssDNA Ligase.

20. The method of claim 16, wherein the DNA nuclease enzyme is 10RecJ Exonuclease or Lambda Exonuclease.

21. The method of claim 16, wherein the RNA acceptor is a miRNA, a siRNA, a piRNA, or a synthetic RNA.

* * * * *

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
gagcggccgc gaagatcaga                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: The residue at this position is linked to a
      3'-amino modifier

<400> SEQUENCE: 2
tcgtatgccg tcttctgctt g                                            21

<210> SEQ ID NO 3
<211> LENGTH: 23
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (18)..(23)
<223> OTHER INFORMATION: n is a, c, g, or t
<220> FEATURE:
<221> NAME/KEY: misc_feature
<222> LOCATION: (23)..(23)
<223> OTHER INFORMATION: The residue at this position is linked to a
      2'-O-methyl group and a C3 spacer moiety

<400> SEQUENCE: 3
gacgaagaca gtagacannn nnn                                             23

<210> SEQ ID NO 4
<211> LENGTH: 22
<212> TYPE: RNA
<213> ORGANISM: Artificial Sequence
<220> FEATURE:
<223> OTHER INFORMATION: Synthetic

<400> SEQUENCE: 4
uucgcuugca gagagaaauc ac                                              22

<210> SEQ ID NO 5
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (21)..(22)
<223> OTHER INFORMATION: n is a, c, g, or u
<220> FEATURE:
<221> NAME/KEY: misc_feature
<222> LOCATION: (22)..(22)
<223> OTHER INFORMATION: The residue at this position is linked to OH

<400> SEQUENCE: 5
nncgcuugca gagagaaauc nn                                              22

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
tcgtatgccg tcttctgctt g                                               21

<210> SEQ ID NO 7
<211> LENGTH: 26
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: The residue at this position is linked to OH

<400> SEQUENCE: 7
guucagaguu cuacaguccg acgauc                                          26
```

```
<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
caagcagaag acggcatacg a                                        21

<210> SEQ ID NO 9
<211> LENGTH: 46
<212> TYPE: DNA
<213> ORGANISM: Artificial Sequence
<220> FEATURE:
<223> OTHER INFORMATION: Synthetic

<400> SEQUENCE: 9
aatgatacgg cgaccaccga caggttcaga gttctacagt ccgacg              46
```